(12) United States Patent
Matsue et al.

(10) Patent No.: US 9,019,301 B2
(45) Date of Patent: Apr. 28, 2015

(54) MEDICAL IMAGE DISPLAY APPARATUS IN WHICH SPECIFICATION OF A MEDICAL IMAGE ENABLES EXECUTION OF IMAGE PROCESSING

(75) Inventors: Kenji Matsue, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1357 days.

(21) Appl. No.: 11/697,905

(22) Filed: Apr. 9, 2007

(65) Prior Publication Data
US 2007/0242069 A1      Oct. 18, 2007

(30) Foreign Application Priority Data
Apr. 12, 2006    (JP) .................................. 2006-109860

(51) Int. Cl.
G09G 5/00       (2006.01)
G06F 19/00      (2011.01)
G06F 3/0486     (2013.01)
(Continued)

(52) U.S. Cl.
CPC .......... *G06F 19/321* (2013.01); *G06F 19/3406* (2013.01); *G06F 19/327* (2013.01); *G06F 19/32* (2013.01); *G06F 19/34* (2013.01); *G06F 3/0486* (2013.01); *G06F 3/04845* (2013.01); *G06F 3/04886* (2013.01)

(58) Field of Classification Search
CPC ......... G06T 11/60; G06T 15/30; G06T 11/40; G06F 19/32; G06F 19/34; G06F 3/0486; G06F 3/04845; G06F 3/04886
USPC ........... 345/619; 382/128–132, 284; 600/407, 600/437
See application file for complete search history.

(56) References Cited

U.S. PATENT DOCUMENTS 6,674,879 B1 *   1/2004   Weisman et al. ............. 382/128
7,155,042 B1 *   12/2006  Cowan et al. ................ 382/128
(Continued)

FOREIGN PATENT DOCUMENTS

JP    2006-6671      1/2006
JP    2006-55522     3/2006

OTHER PUBLICATIONS

Office Action issued May 17, 2011, in Japanese Patent Application No. 2006-109860.

*Primary Examiner* — Jin-Cheng Wang
(74) *Attorney, Agent, or Firm* — Oblon, McClelland, Maier & Neustadt, L.L.P.

(57) ABSTRACT

A medical image display apparatus 1 having a display component 9, an image data storage part 31, an information storage component 32, an operation component 10, and a control part 2. The display component 9 displays a medical image display screen P on which image display regions P1 to P4 are defined. The image data storage part 31 stores image data of medical images. The information storage component 34 stores process associating information 32a for associating combinations of the image display regions P1 to P4 with the processing content of image data of medical images. The control part 2, when two medical images displayed on different image display regions of the image display regions P1 to P4 have each been designated using the operation component 10, instructs to execute, for at least one image data of said two medical images, the process indicated in the processing content associated with the combination of the image display regions in which these two medical images are displayed by the process associating information 32a.

43 Claims, 25 Drawing Sheets

(51) Int. Cl.
*G06F 3/0484* (2013.01)
*G06F 3/0488* (2013.01)

(56) References Cited

U.S. PATENT DOCUMENTS

| | | | |
|---|---|---|---|
| 7,162,068 B2* | 1/2007 | Akagi | 382/132 |
| 7,545,967 B1* | 6/2009 | Prince et al. | 382/130 |
| 7,597,663 B2* | 10/2009 | Wang et al. | 600/437 |
| 7,899,684 B2* | 3/2011 | Fukatsu et al. | 705/2 |
| 2002/0059315 A1* | 5/2002 | Sumita et al. | 707/200 |
| 2003/0031380 A1* | 2/2003 | Song | 382/284 |
| 2003/0060678 A1* | 3/2003 | Watai et al. | 600/109 |
| 2003/0142119 A1* | 7/2003 | Akagi | 345/698 |
| 2005/0143641 A1* | 6/2005 | Tashiro | 600/407 |
| 2005/0259116 A1* | 11/2005 | Araoka | 345/619 |
| 2006/0058625 A1* | 3/2006 | Mori | 600/407 |
| 2006/0064321 A1* | 3/2006 | Sasano et al. | 705/2 |
| 2006/0085407 A1* | 4/2006 | Kaminaga et al. | 707/3 |
| 2006/0168338 A1* | 7/2006 | Bruegl et al. | 709/240 |
| 2006/0170765 A1* | 8/2006 | Akimoto et al. | 348/45 |
| 2008/0009669 A1* | 1/2008 | Ozawa et al. | 600/101 |

* cited by examiner

FIG. 3

Processed content associated information 32a

To which to drag and drop

| From which to drag and drop \ To which to drag and drop | Display region of the medical image display screen | Thumbnail display region P1 | Observation image display region P2 | Thumbnail display region P3 | Observation image display region P4 |
|---|---|---|---|---|---|
| | Thumbnail display region P1 | — | (1) Display image switch processing<br>(2) Parallel display processing | — | (1) Tomorogrphic image generation processing<br>(2) Approximate section selection processing<br>(3) Fusion image generation processing |
| | Observation image display region P2 | — | — | (1) Series synchronization processing<br>(2) Difference image generation processing | — |
| | Thumbnail display region P3 | (1) Series synchronization processing<br>(2) Difference image generation processing | — | — | (1) Display image switch processing<br>(2) Parallel display processing |
| | Observation image display region P4 | (1) Tomographic image generation processing<br>(2) Approximate section selection processing<br>(3) Fusion image generation processing | (1) Annotation attachment processing<br>(2) Measurement attachment processing | — | — |

FIG. 22

|  | Image G1 | Image G2 | Image G3 | .... | .... | Image Gh |
|---|---|---|---|---|---|---|
| Image G1 |  | s(1, 2) | s(1, 3) | .... | .... | s(1, h) |
| Image G2 | s(2, 1) |  | s(2, 3) | .... | .... | s(2, h) |
| Image G3 | s(3, 1) | s(3, 2) |  | .... | .... | s(3, h) |
| .... | .... | .... | .... | .... | .... | .... |
| .... | .... | .... | .... | .... | .... | .... |
| Image Gh | s(h, 1) | s(h, 2) | s(h, 3) | .... | .... |  |

MEDICAL IMAGE DISPLAY APPARATUS IN WHICH SPECIFICATION OF A MEDICAL IMAGE ENABLES EXECUTION OF IMAGE PROCESSING

BACKGROUND OF THE INVENTION

1. Field of the Invention

The present invention relates to a medical image display apparatus for conducting interpretation of a medical image obtained by a medical image diagnosis apparatus.

2. Description of the Related Art

Conventional medical image diagnosis apparatuses have been widely used for obtaining medical images. Such medical image diagnosis apparatuses include an X-ray diagnosis apparatus, an X-ray CT apparatus, an MRI apparatus, a nuclear medical diagnosis apparatus (e.g. a positron emission computed tomography apparatus, a single photon emission computed tomography apparatus), and an ultrasound diagnosis apparatus, and so on.

The obtained medical image will be displayed on the medical image display apparatus and provided for interpretation. Incidentally, a system configured to save the obtained medical image in a database and download the desired medical image from the database to the medical image display apparatus has also been put into practical use.

Such medical image display apparatuses include 2D viewers capable of displaying only two-dimensional medical images and 3D viewers capable of also displaying 3-dimensional medical images. Herein, the three-dimensional medical images are pseudo three-dimensional images generated by creating volume data with layers of a plurality of tomographic images and rendering this volume data.

The medical image display apparatus is equipped with various types of functions for improving the accuracy of interpretation or diagnosis, facilitating work, and so on. Examples of such functions include the following: a function for displaying medical images by unit of study, series, and image; function for enlarging, reducing, rotating and panning images; a function for measuring distance, planar dimension, and angle (such as a bone and an affected area) in medical images (e.g., cf. Japanese Unexamined Patent Application Publication No. 2004-8535); and a function for inputting an annotation (such as arrows, graphics, and characters) into medical images (e.g., cf. Japanese Unexamined Patent Application Publication No. 2004-8535).

Incidentally, in systems compliant with DICOM (Digital Imaging and Communication in Medicine), the standard for digital medical images, medical images are managed hierarchically such as an upper-level hierarchy "Study," mid-level hierarchy "Series," and lower-level hierarchy "Image."

In addition, 3D viewers are equipped with the following functions: a function for performing rotation or the like to the volume data; function for displaying a MPR (MultiPlanar Reconstruction) image based on the volume data (e.g., cf. Japanese Unexamined Patent Application Publication No. 2006-127); a function for displaying an oblique image based on the volume data (e.g., cf. Japanese Unexamined Patent Application Publication No. H8-212391); and a function for capturing a displayed image as a two-dimensional image. The captured image will be stored as a new series belonging to that study. Incidentally, an oblique image refers to a cross-sectional image inclining at any angle to the slice plane.

These functions are designed to be selectively executed by a user operating various types of software keys, such as buttons displayed on the screen, using a mouse or the like.

When conducting interpretation work with the medical image display apparatus, software keys are also displayed on the screen on which the medical image is displayed. Therefore, a disadvantage has occurred wherein, when displaying a medical image with large size on the display screen, the software keys are displayed overlapping the medical image and therefore part of the image cannot be observed.

Incidentally, avoiding this overlapping display of the software keys requires an arrangement in which the software keys are arranged at the peripheral edge of the display screen and medical images are displayed in the other separate display region. However, the size of the displayed medical image is reduced, disadvantageously making it more difficult to observe the details of the medical image or the like.

Herein, it is also conceivable to enlarge the display region of the medical image by enlarging the screen size of the display, or by scroll display of the medical image, and so on. However, the former results in increased cost or the like and the latter causes disadvantages such as complicating the observation work. Therefore, these remedies are far from an acceptable solution from the viewpoint of the users.

In addition, it is also conceivable not to display the software keys during the interpretation work, whereby the software keys are displayed by conducting a predetermined operation when the above functions are used. However, for that purpose, the following procedure is required: (1) display the software keys, (2) perform the desired function with the software keys, and (3) hide the software keys. Therefore, a problem occurs in that the operating procedure becomes more complicated compared to the traditional configuration in which only step (2) is performed.

SUMMARY OF THE INVENTION

The present invention is intended to solve such problems, with the purpose of providing a medical image display apparatus for solving disadvantages due to a software key on the display screen during observation of medical images.

In addition, another object of the present invention is to provide technology for avoiding complication of the operation procedure of the medical image display apparatus.

The first embodiment of the present invention is a medical image display apparatus comprising: a display component operable to display a medical image display screen on which a plurality of image display regions are preliminarily defined, an image data storage component operable to store image data of medical images, an associating information storage component operable to store associating information associating a combination of said image display region with a processing content to the image data of the medical images, an operation component, and a control component operable to instruct to execute processing on image data of one or more medical images of at least two medical images based on the combination of image display regions of said at least two medical images and said associating information, when said at least two medical images displayed on different image display regions of said plurality of image display regions are designated respectively using said operation component.

According to this first embodiment, the processing that has conventionally been executed by operating software keys can be performed by specifying a medical image, so there is no need to display the software keys for execution of processing on the medical image display screen.

As a result, it is possible to solve the disadvantages resulting from the software keys being displayed on the medical image display screen. Particularly, it is possible to avoid a situation where a portion of the medical image cannot be observed due to display of the software keys. In addition, it is not necessary to reduce the display size of the medical image so as not to overlap with the software keys. In addition, because performing only the simple operation of specifying a medical image enables execution of the desired processing, operationality does not become complicated.

The second embodiment of the present invention is a medical image display apparatus comprising: a display component operable to display a medical image display screen on which a plurality of image display regions is preliminarily defined, an image data storage component operable to store image data of medical images, an associating information storage component operable to store associating information associating a combination of said image display region with a processing content to the image data of the medical images, an operation component, and a control component operable to instruct when the medical images respectively displayed in first image display region group of said plurality of image display regions and second image display region group are designated using said operation component, to execute the process to image data of said designated medical image based on the combination of said first image display region group and said second image display region group and said associating information.

According to the second embodiment, simply specifying a medical image and an image display region enables execution of the processing that was conventionally executed by operation of the software keys. Therefore, there is no need to display software keys for execution of processing on the medical image display screen. As a result, it is possible to solve the disadvantages resulting from the software keys being displayed on the medical image display screen. In addition, because performing only the simple operation of specifying a medical image enables execution of the desired processing, operationality does not become complicated.

BRIEF DESCRIPTION OF THE DRAWINGS

FIG. 3 is a diagram showing one example of process associating information for one embodiment of the medical image display apparatus according to the present invention.

FIG. 22 is a diagram showing one example of a screen displayed by a modification example of one embodiment of the medical image display apparatus according to the present invention.

DETAILED DESCRIPTION OF THE PREFERRED EMBODIMENTS

Example embodiments of the medical image display apparatus according to the present invention will be described in detail with reference to the drawings.

Apparatus Configuration

Figure 1:
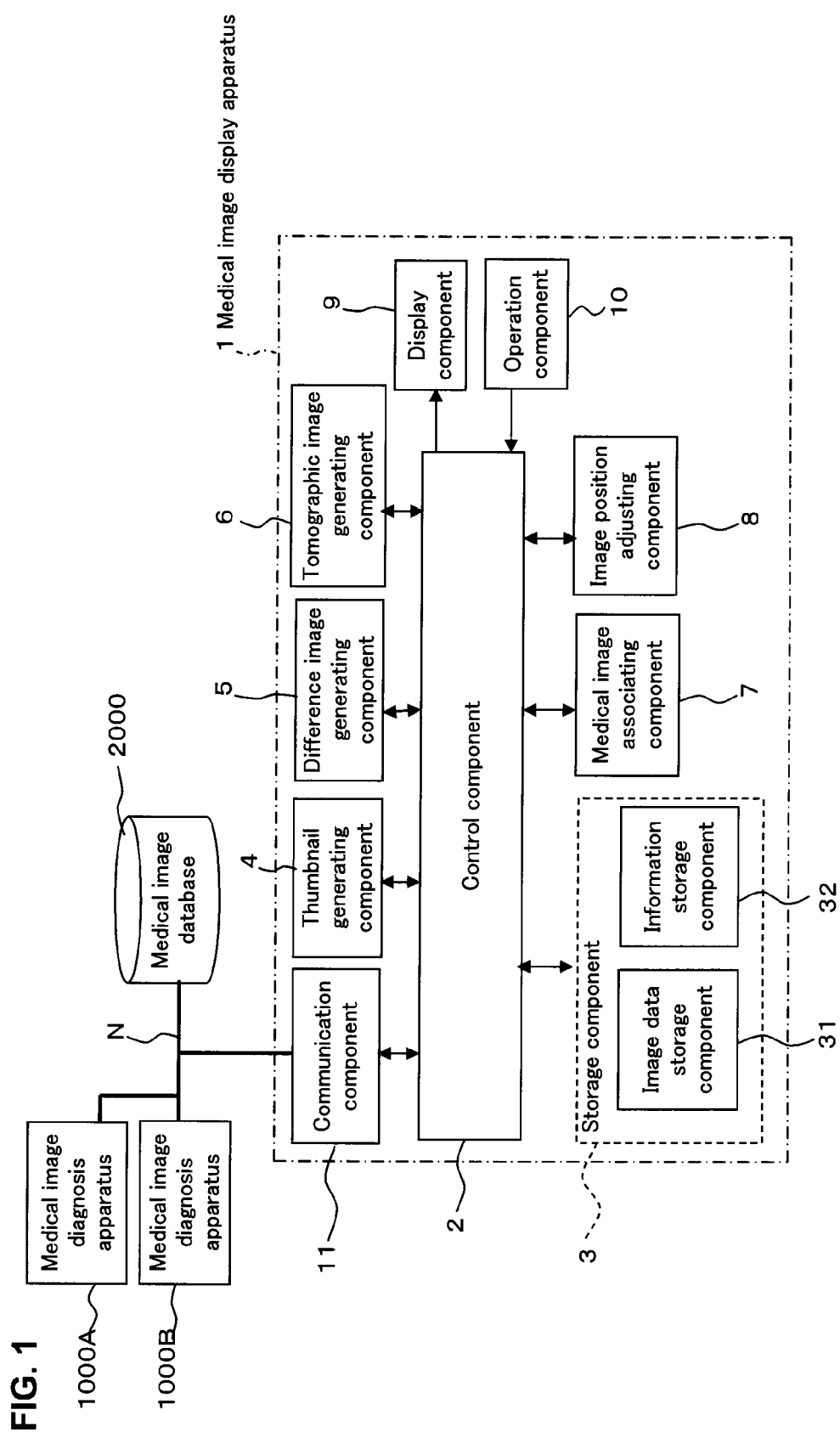
FIG. 1 is a block diagram showing one example of the entire configuration of one embodiment of the medical image display apparatus according to the present invention.

One example of the entire configuration of the medical image display apparatus according to the present invention is shown in FIG. 1. The medical image display apparatus 1 shown in FIG. 1 is an apparatus used to conduct interpretation of medical images and generally referred to as a medical image viewer or the like. The medical image display apparatus 1 is connected to medical image diagnosis apparatuses (modalities) 1000A and 1000B or a medical image database 2000 via a network N such as LAN (Local Area Network). The medical image display apparatus 1, the medical image diagnosis apparatuses 1000A and 1000B, and the medical image database 2000 form a system compliant with, for example, DICOM standard.

The medical image diagnosis apparatuses 1000A and 1000B each consist of any medical image diagnosis apparatuses used for obtaining medical images such as an X-ray diagnosis apparatus, an X-ray CT apparatus, an MRI apparatus, a nuclear medical diagnosis apparatus, and an ultrasound diagnosis apparatus. In addition, hybrid modality such as PET-CT can be used as the medical image diagnosis apparatuses 1000A and 1000B. Image data for medical images obtained by the medical image diagnosis apparatuses 1000A and 1000B are sent to and kept in the medical image database 2000.

The medical image database 2000 is constituted to include a storage unit for saving image data for medical images and application software for managing the image data saved in this storage unit. This storage unit consists of a high-capacity hard disk drive or the like. As a medical image database 2000, PACS (Picture Archiving and Communication System) or the like is generally used. The medical image display apparatus 1 is designed to accordingly read out the image data kept in the medical image database 2000 and to display the medical image.

Next, the internal configuration of the medical image display apparatus 1 is described. The medical image display apparatus 1 is constituted to include a control component 2, a storage component 3, a thumbnail generating component 4, a difference image generating component 5, a tomographic image generating component 6, a medical image associating component 7, an image position adjusting component 8, a display component 9, an operation component 10, and a communication component 11.

Control Component

The control component 2 controls each part of the medical image display apparatus 1. The control component 2 is constituted to include, for example, a microprocessor such as CPU (Central Processing Unit), a main memory such as RAM, and an external storage unit such as a hard disk drive. A computer program (not shown) for execution the processing explained in the present embodiment by the medical image display apparatus 1 has been saved in this external storage unit in advance. The microprocessor controls each part of the apparatus by loading this computer program into the main memory and by executing it. The control component 2 is included in one example of the "control component" of the present invention.

Storage Component

The storage component 3 is constituted to include storage units such as a hard disk drive for storing various types of data. The storage component 3 is provided with an image data storage component 31 and an information storage component 32. The image data storage component 31 stores image data for medical images. The information storage component 32 stores information to be served for processing by the medical image display apparatus 1. Herein, the image data storage component 31 and the information storage component 32 may be formed as different storage regions of a single storage unit, or may each consist of individual storage units. The image data storage component 31 is included in one example of the "image data storage component" of the present invention. The information storage component 32 is included in one example of the "associating information storage component" of the present invention.

Figure 2:
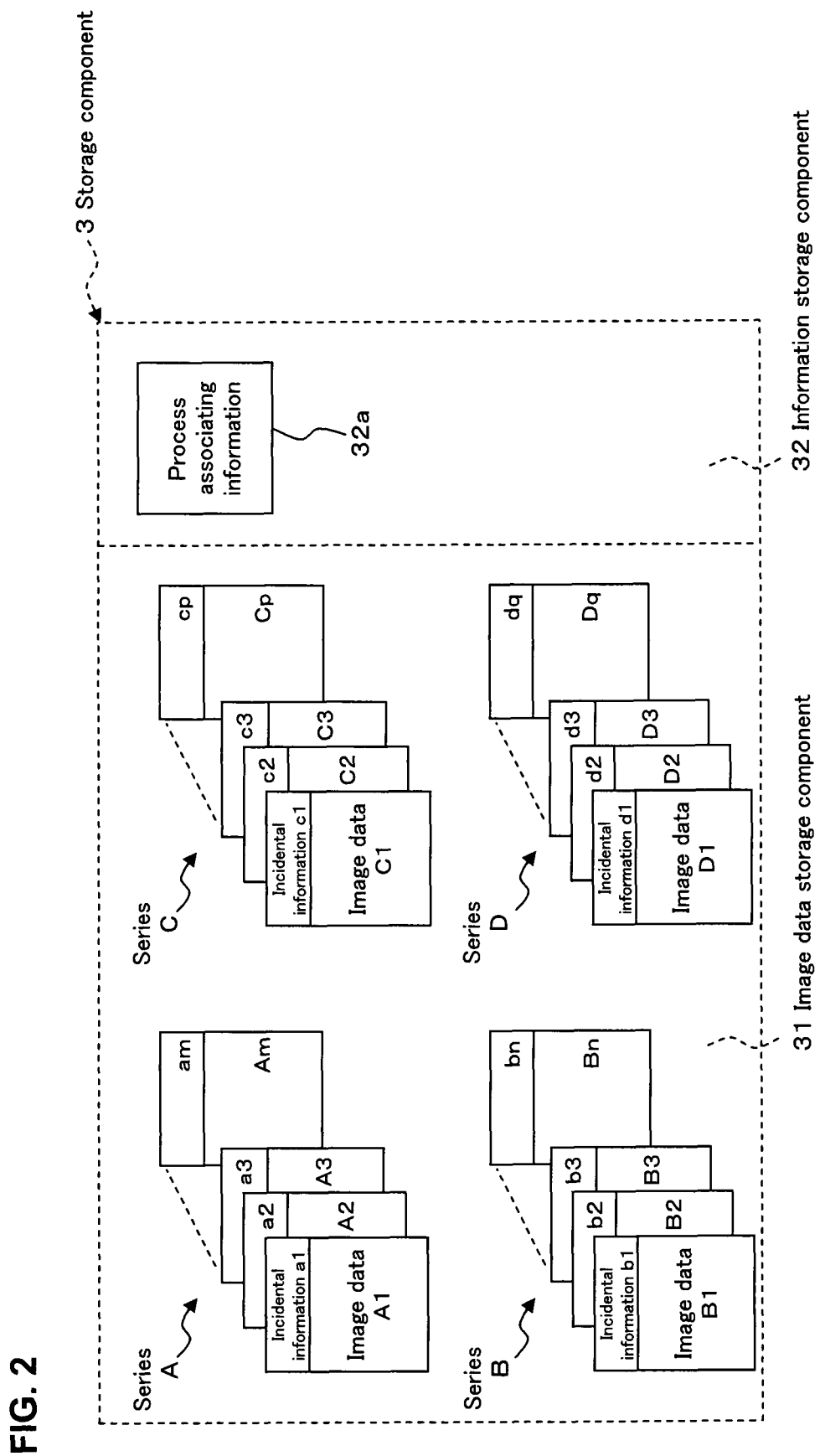
FIG. 2 is a diagram showing one example of information stored in the storage component of one embodiment of the medical image display apparatus according to the present invention.

One example of the data to be stored in the storage component 3 is shown in FIG. 2. The image data for medical images from series A, B, C, and D are stored in the image data storage component 31 of the storage component 3 shown in FIG. 2. The image data for medical images from series A is equivalent to a series of medical images, for example, obtained by a single scan of the medical image diagnosis apparatus 1000A (1000B). The image data for medical images from series A includes image data A1, A2, A3, . . . , and Am of this series of medical images. Similarly, the image data for medical images from series B includes image data B1, B2, B3, . . . , and Bn of the series of medical images. In addition, the image data for medical images from series C includes image data C1, C2, C3, . . . , and Cp of the series of medical images. In addition, the image data for medical images from series D includes image data D1, D2, D3, . . . , and Dq of the series of medical images.

In addition, the image data A1, A2, A3, . . . , and Am from series A are each attached by the incidental information a1, a2, a3, . . . , and am. The incidental information a1 to am are the information attached to image data based on, for example, the DICOM standard. The incidental information a1 to am store series ID information, medical image ID information, study order information, modality type information, imaging date and time information, patient information, image position information, imaging condition information, imaging phase information, annotation information, measurement information, and so on.

Herein, series ID information is information for identifying the series to which the medical image belongs. In addition, medical image ID information is information for identifying the medical image. In addition, study order information is identification information for ordering to obtain the medical image.

In addition, the modality type information is information used for identifying the modality by which the medical image was obtained, such as X-ray CT or MRI. In addition, the imaging date and time information is information indicating the date and time when the medical image was taken. In addition, the patient information is information such as patient ID for identifying the patient who is the subject of the medical image.

In addition, the image position information is information indicating the imaging position of the medical image, for example, information based on the coordinate system set on the medical image according to modality. This image position information includes, for example in the case of a tomographic image, cross-sectional position information indicating the cross-sectional position (coordinates) in the scanning direction and cross-sectional direction information indicating the cross-sectional direction. Incidentally, tomographic images are not limited to linearly arranged tomographic images obtained by linear scanning with a medical image diagnostic apparatus such as an X-ray CT. For example, they may be the tomographic images obtained by, for example, circular scanning with a medical image diagnosis apparatus such as an ultrasound diagnosis apparatus and arranged along any circular orbit or the like. In this case, the "cross-sectional direction" may be equivalent to the direction in which the tomographic image is arranged (for circular arrangement, the tangential direction of the circular orbit).

In addition, the imaging condition information is information indicating the imaging condition when the medical image was taken. Imaging condition may include the scanning method, the slice width, the window level, the window width, and so on. In addition, the imaging phase information is attached to medical images representing time changes in the site to be obtained such as an ECG gated scan. This imaging phase information is information indicating the phase when the medical image was obtained.

In addition, the annotation information is information regarding annotations attached to the medical image, such as arrows, graphics, and characters. This annotation information includes, for example, image data and text data for annotations. This text data includes information regarding the position and size to which annotation would be attached. In addition, the measurement information is information indicating the results of distance, planar dimension, and angle measurements of the medical image. This measurement information includes information such as the measurement type and the position and size of the measured image.

Process associating information 32a is stored in the information storage component 32. One example of the process associating information 32a is shown in FIG. 3. The process associating information 32a is information associating a combination of image display regions on the medical image display screen P shown in FIG. 4 with the processed content for image data for the medical image.

Medical Image Display Screen

The configuration of the medical image display screen P will be described prior to explaining the process associating information 32a. The medical image display screen P has a thumbnail display region P1, an observation image display region P2, a thumbnail display region P3, and an observation image display region P4. Herein, the thumbnail display regions P1 and P3 respectively are included in one example of the "reduced image display region" of the present invention. In addition, one of the thumbnail display regions P1 and P3 is included in one example of the "first reduced image display region", and the other is included in one example of the "second reduced image display region". In addition, one of the observation image display regions P2 and P4 is included in one example of the "first observation image display region", and the other is included in one example of the "second observation image display region". A two-dimensional coordinate system is preset on the medical image display screen P. For each display region P1 to P4, the ranges and positions are specified by this two-dimensional coordinate system.

For example, a thumbnail g1 of a medical image included in the series for present interpretation is displayed on the thumbnail display region P1. The thumbnail g1 is a thumbnail of the medical image (referred to as the "representative image") representing the multiple medical images that form that series. The representative image can be the medical image that was first obtained in the series of medical images, or a medical image at a predetermined image position (such as a cross-sectional position), and so on. For example, when displaying a thumbnail representing series A shown in FIG. 2, a thumbnail based on any one image of the image data A1 to Am of this series A will be displayed in the thumbnail display region P1. Herein, "representative" does not mean that it characteristically represents the series of medical images, but simply means that it was arbitrarily selected from a series of medical images in order to generate the image data for the thumbnail.

An observation image G1 of a medical image is displayed on the observation image display region P2. The observation image G1 is included in the series represented by the thumbnail g1 displayed on the thumbnail display region P1. In addition, observation images of a plurality of medical images of that series can be sequentially displayed by the predetermined operation using the operation component 10. For example, for series A of FIG. 2, observation images based on the image data A1 to Am can be sequentially displayed. Incidentally, "observation image" may mean an image displayed for a user (diagnostic reading doctor) to observe the medical image.

For example, thumbnails g2 and g3 of the medical images are displayed in the thumbnail display region P3. The thumbnails g2 and g3 represent the series to be compared with the present series for interpretation. This series to be compared can include, for example, a medical image obtained previously at the same site as the present series for interpretation (for progress observation, preoperative and postoperative observation, and so on).

An observation image G2 (and/or an observation image G3 (not shown)) of a medical image is displayed on the observation image display region P4 similarly to the observation image display region P2. The observation image G2 (and/or an observation image G3) is included in the series represented by thumbnail g2 (and/or the thumbnail g3) displayed in the thumbnail display region P3.

Figure 4:
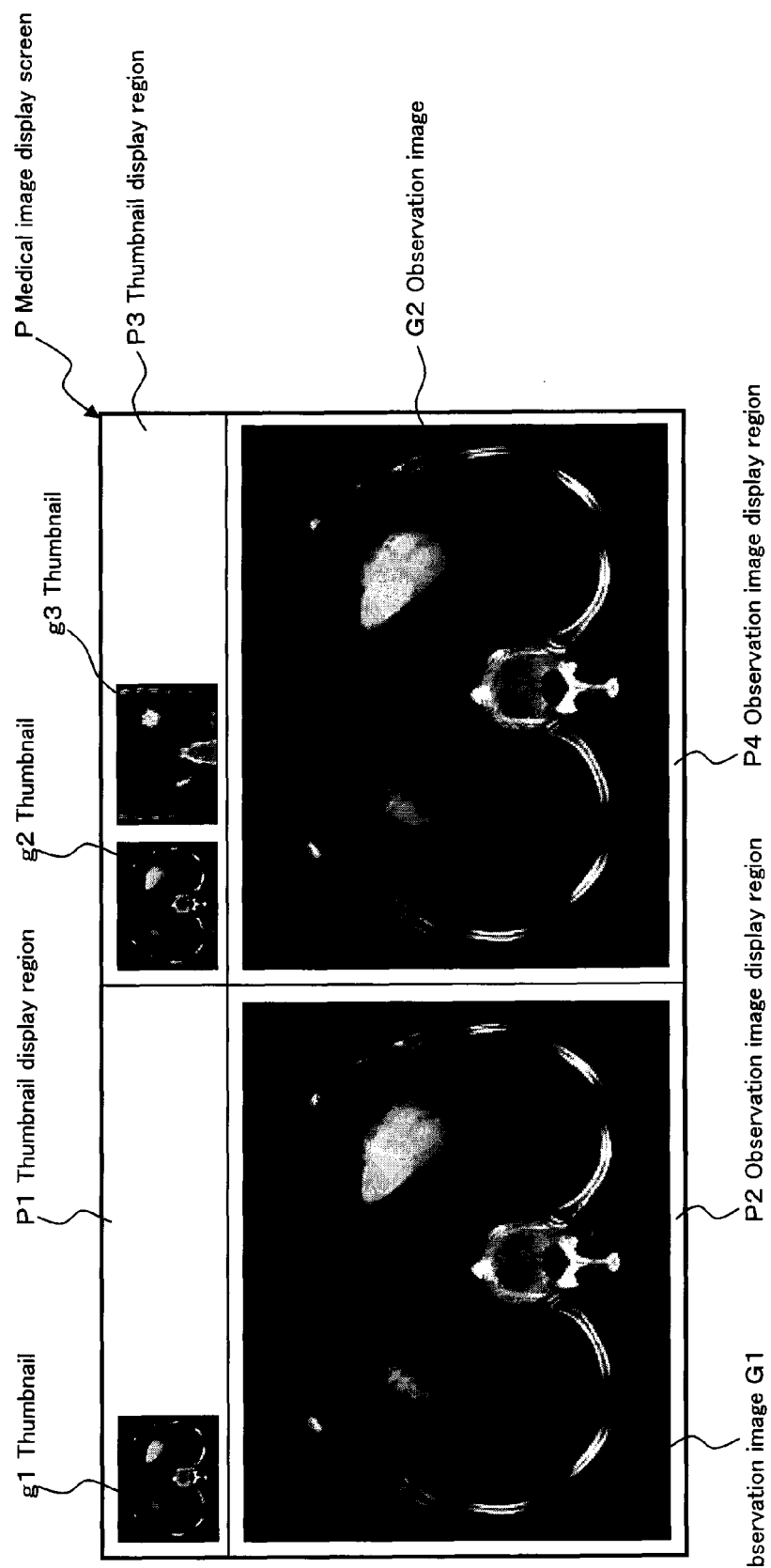
FIG. 4 is a diagram showing one example of display feature of the medical image display apparatus according to the present invention.
Figure 5:
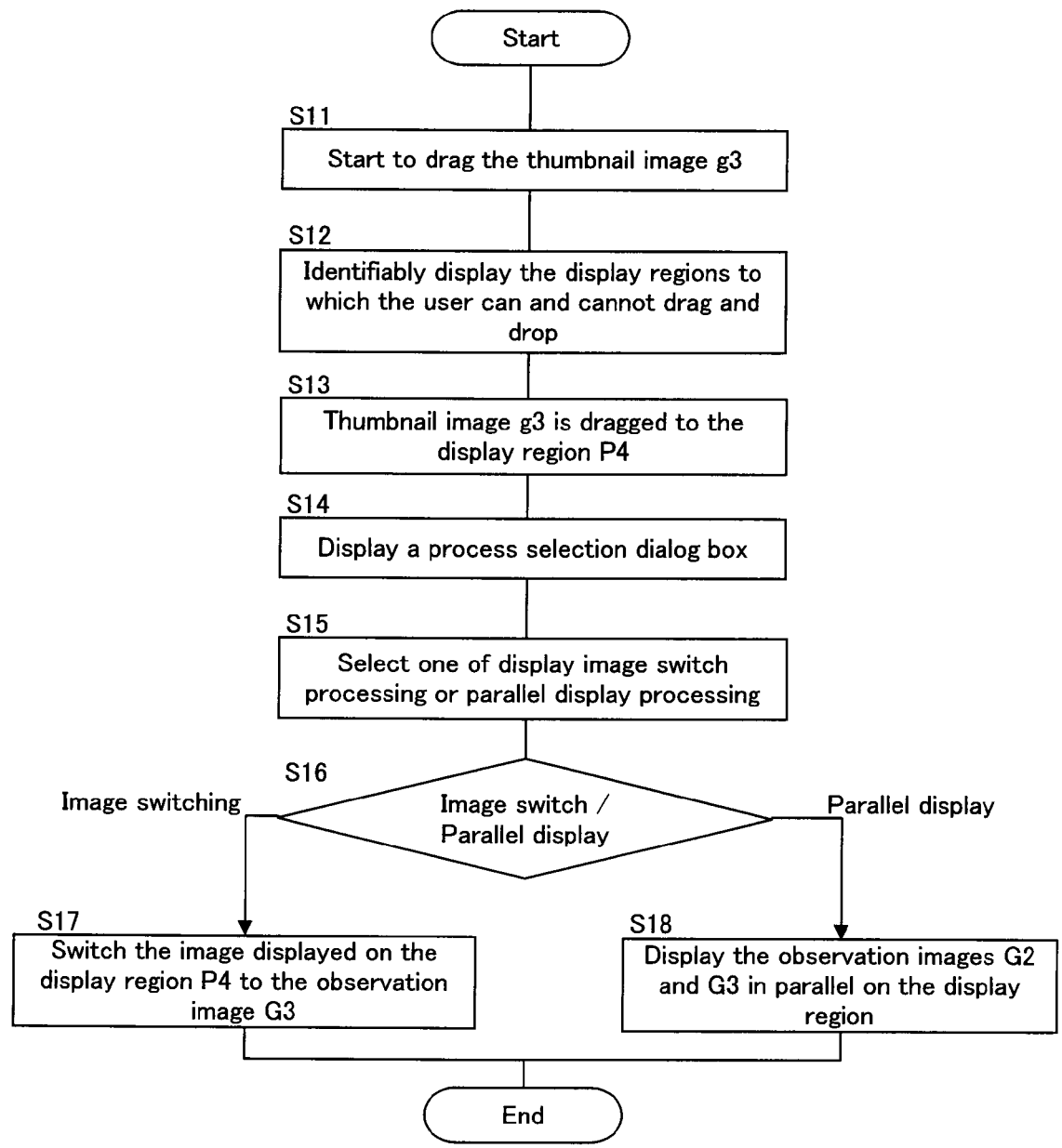
FIG. 5 is a flow chart showing one example of processing performed by one embodiment of the medical image display apparatus according to the present invention.

In this way, the medical image display screen P shown in FIG. 4 is designed to display a medical image of the series for present interpretation (thumbnails and observation images) on the left side of the screen and to display a medical image of the series to be compared therewith (thumbnails and observation images) on the right side of the screen.

Process Associating Information

The process associating information 32a of FIG. 3 is described. The process associating information 32a is included in one example of the "associating information" of the present invention. The process associating information 32a associates a combination of any two or more of the thumbnail display region P1, the observation image display region P2, the thumbnail display region P3, and the observation image display region P4 with the processing contents to be executed on the image data for the medical images. Herein, each display region P1 to P4 is specified by coordinates in a preset two-dimensional coordinate system on the medical image display screen P (display screen of the display component 9).

Incidentally, the process associating information 32a shown in FIG. 3 is specifically used with a mouse provided as an operation component 10. At this time, medical images or display regions will be designated by a drag and drop operation with the mouse. In addition, (images displayed in) the display regions P1 to P4 will be specified by the coordinates of the position on the medical image display screen P designated by a mouse or the like.

The content defined in the process associating information 32a will now be specifically described. First, (1) display image switch processing and (2) parallel display processing, are associated by the combination of the thumbnail display region P1 and the observation image display region P2 (order of designation is only as follows: P1→P2).

In addition, (1) synchronization between series processing and (2) difference image generating processing, are associated with the combination of the thumbnail display region P1 and the thumbnail display region P3 (in any order of designation).

In addition, (1) tomographic image generating processing, (2) approximate section selecting processing, and (3) fusion image generating processing, are associated with the combination of the thumbnail display region P1 and the observation image display region P4 (in any order of designation).

In addition, (1) display image switch processing and (2) parallel display processing, are associated with the combination of the thumbnail display region P3 and the observation image display region P4 (order of designation is only as follows: P3→P4).

In addition, (1) annotation attaching processing and (2) measurement attaching processing, are associated with the combination of the observation image display region P4 and the observation image display region P2 (order of designation is only as follows: P4→P2). The specific processing content defined in the process associating information 32a will be described later.

Thumbnail Generating Component

The thumbnail generating component 4 generates image data for a thumbnail of a medical image based on image data for this medical image. As a generating method of thumbnails, any conventional method can be used accordingly. The thumbnail generating component 4 is included in one example of the "reduced image generating component" of the present invention. The thumbnail generating component 4 is constituted to include a microprocessor or the like for executing the predetermined computer program.

Difference Image Generating Component

The difference image generating component 5 generates image data for a difference image between two medical images based on image data for these two medical images. As a generating method of difference images, any traditional way, such as subtracting pixel values of one image data from pixel values another image data can be accordingly used. The difference image generating component 5 is included in one example of the "difference image generating component" of the present invention. The difference image generating component 5 is constituted to include a microprocessor or the like for executing the predetermined computer program.

Tomographic Image Generating Component

The tomographic image generating component 6 generates image data for a tomographic image of the cross-sectional direction different from a plurality of tomographic images of an object based on image data for this plurality of tomographic images. The processing performed by the tomographic image generating component 6 may be, for example, MPR, oblique image generating processing, and so on. The tomographic image generating component 6 is included in one example of the "tomographic image generating component" of the present invention. The tomographic image generating component 6 is constituted to include a microprocessor or the like for executing the predetermined computer program.

MPR is the processing to generate image data for a tomographic image of another cross-sectional direction, based on image data from a plurality of tomographic images in a certain cross-sectional direction. For example, MPR processing may be to generate image data for a coronal image or sagittal image based on image data from a plurality of axial images of an object. Incidentally, when implementing MPR for a tomographic image in which the slice width is large relative to the pixel size in the slice plane, such as a CT image, it is preferable to firstly generate volume data (voxel data) through interpolation of image data from a plurality of tomographic images and generate image data from the objective tomographic image based on this volume data.

In addition, the oblique image generating processing is the processing for generating image data for a tomographic image of arbitrary cross-sectional direction based on image data for a plurality of tomographic images of a certain cross-sectional direction. In this case, it is possible to generate volume data and then image data for the tomographic image of the objective cross-sectional direction as well.

Medical Image Associating Component

The medical image associating component 7 associates medical images belonging to a certain series with medical images belonging to another series based on incidental information for these medical images.

More specifically, the medical image associating component 7, for example, refers to image position information included in incidental information for medical images of each series, so that medical images whose positions are almost identical of different series are associated with each other. Particularly, when the medical image is a tomographic image, the medical image associating component 7 refers to the cross-sectional position information for the incidental information of each series so that tomographic images whose cross-sectional positions are almost identical of different series are associated with each other.

A case will now be described in which the medical image in each series is a temporal image such as an ECG synchronization image. In this case, the medical image associating component 7 refers to the imaging phase information included in the incidental information of the medical images in each series. Thereby, a medical image from one series in which imaging phases indicated in their imaging phase information are almost identical is associated with a medical image from another series.

Herein, "almost identical (substantially identical)" shall mean the range permitting misalignment that is not detrimental to the precision during comparing and observing the associated two medical images. This range of "almost identical" can be set accordingly depending on various types of conditions such as precision and observation sites of the medial images. In addition, for a certain medical image from one series, a medical image whose position or phase is closest to the above certain medical image, is selected from another series and associate to the above medical image (such case shall also be included in the range of "almost identical").

The medical image associating component 7 is included in one example of the "medical image associating component" of the present invention. The medical image associating component 7 is constituted to include a microprocessor or the like for executing the predetermined computer program. In addition, the medical image associating component 7 is included in the "control component" of the present invention.

Image Position Adjusting Component

The image position adjusting component 8 adjusts positions of different kinds of a plurality of medical images based on image data for these medical data and their image position information.

Herein, "different kinds of medical images" indicate medical images that have been obtained by different modality or medical images that have been obtained by different imaging method. For example, a CT image obtained with an X-ray CT apparatus and a PET image obtained with PET are examples of medical images obtained by each different modality. In addition, an image of the internal morphology of an object obtained by an MRI apparatus and a functional image of the object obtained by an MRI apparatus are examples of medical images obtained by each different imaging method.

The "position adjustment of the medical image" is performed such that coordinates indicated in image position information for each medical image coincide with each other. In addition, when each medical image has a common characteristic site, the position adjustment can be performed such that the position of this characteristic site coincide with each other.

The control component 2 instructs the display component 9 to display the medical images overlapping with each other to which the image position adjusting component 8 has adjusted position. At this time, the control component 2 instructs to display the images so as to enable visual contact with both the upper image and the lower image, such as by adjusting the transparency value of the overlapping image. Such an image is referred to as a "fusion image" (e.g., cf. Japanese Unexamined Patent Application Publication No 2005-334634).

The image position adjusting component 8 is included in one example of the "image position adjusting component" of the present invention. The image position adjusting component 8 is constituted to include a microprocessor or the like for executing the predetermined computer program.

Display Component

The display component 9 consists of display apparatus in any form such as a LCD (Liquid Crystal Display) and a CTR display (Cathode Ray Tube Display). The display component 9 is included in one example of the "display component" of the present invention.

Operation Component

The operation component 10 consists of any operation apparatus and input apparatus. The operation component 10 may be a mouse, a track ball, a keyboard, a control panel, a joy stick, and so on. The operation component 10 is included in one example of the "operation component" of the present invention.

Incidentally, the display component and the operation component are separated in the present embodiment, but not limited to this. For example, it is also possible to use an apparatus such as a touch panel LCD in which the display component and the operation component are incorporated.

Communication Component

The communication component 11 communicates information through a network N. The communication component 11 is constituted to include communication units such as a LAN card and a MODEM. The communication component 11 is included in one example of the "communication component" of the present invention.

Action

Actions of the medical image display apparatus 1 of the present embodiment are described. FIG. 5 to FIG. 20 are drawings for illustrating one example of actions of the medical image display apparatus 1.

First, (the predetermined computer program of) the medical image display apparatus 1 is activated. The control component 2 instructs the display component 9 to display the predetermined patient list screen (not shown). When a user (diagnostic reading doctor) selects a desired patient by operating the operation component 10, the control component 2 will instruct the display component 9 to display the medical image display screen P for the selected patient.

The medical image display screen P at this time may display only a thumbnail or may also display an observation image as shown in FIG. 4. Herein, it is described assuming that the medical image display screen P shown in FIG. 4 is displayed.

Display Image Switch Processing and Parallel Display Processing

The display image switch processing and the parallel display processing will now be described. Herein, the description refers to the flow chart in FIG. 5 and the drawings showing the display features of the medical image display screen P in FIG. 6 to FIG. 10. The processing operations are executed by dragging and dropping the thumbnail displayed on the thumbnail display region P1 (or P3) into the observation image display region P2 (or P4) as shown in the process associating information 32*a* of FIG. 3.

Hereinafter, it is assumed that processing is executed by dragging and dropping the thumbnail g3 of the thumbnail display region P3 into the observation image display region P4 as shown in FIG. 4.

First, a mouse pointer MP is pointed at the thumbnail g3 by operating the mouse of the operation component 10 on the medical image display screen P as shown in FIG. 4. When dragging of the thumbnail g3 starts (S11), the control component 2, with reference to the process associating information 32*a*, instructs to display the display region associated with the thumbnail display region P3 and the display region not associated with the same, in identifiable display feature respectively (S12). The thumbnail g3 is displayed on the thumbnail display region P3. At this time, the control component 2 specifies the thumbnail display region P3 with the coordinates on the medical image display screen P where the mouse pointer MP is located when dragging starts (hereinafter same as above).

Figure 6:
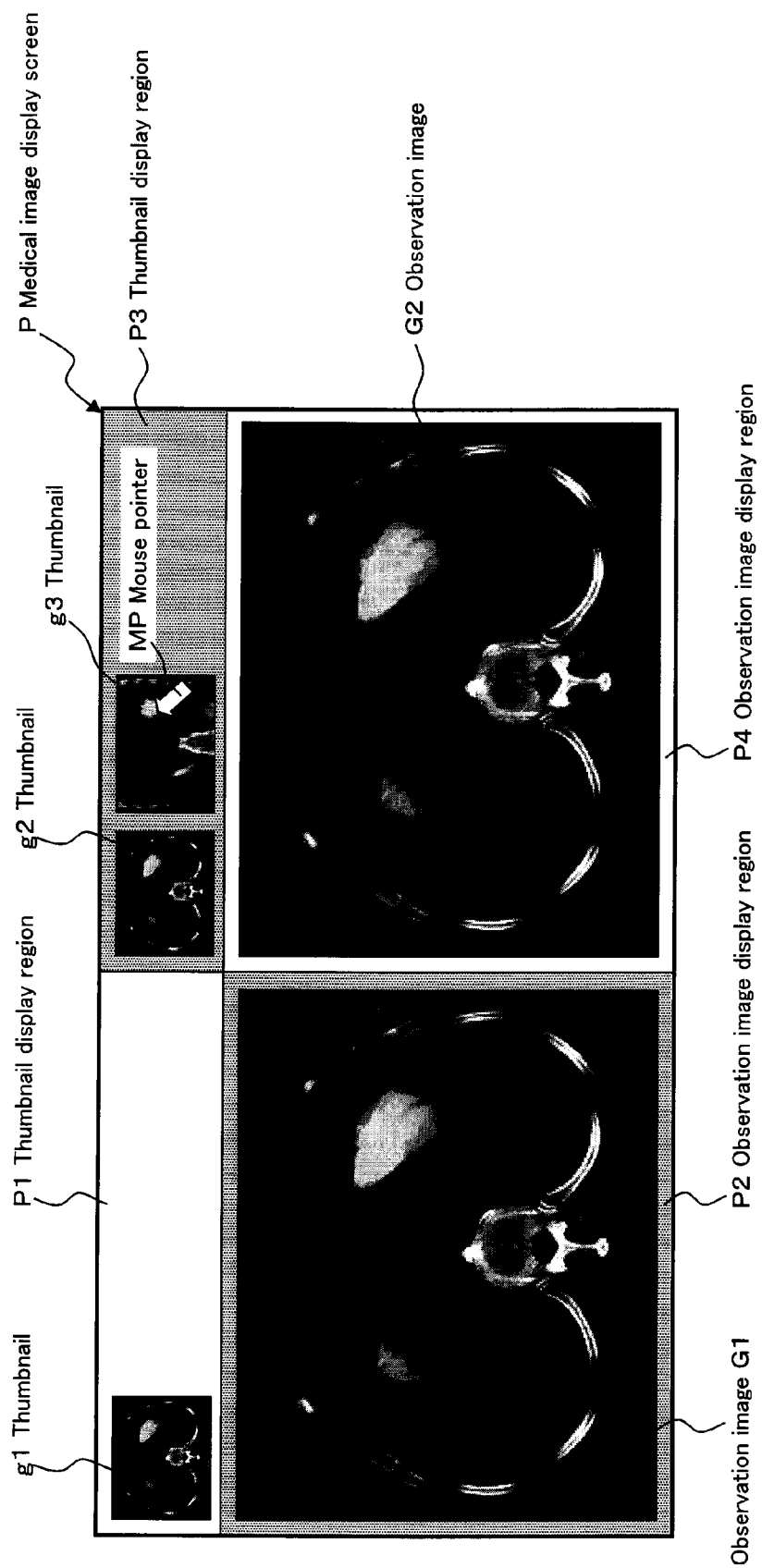
FIG. 6 is a diagram showing one example of display feature of the medical image display screen according to one embodiment of the medical image display apparatus according to the present invention.

In the present embodiment, the display regions associated with the thumbnail display region P3 are the thumbnail display region P1 and the observation image display region P4. On the other hand, the display regions not associated with the thumbnail display region P3 are the observation image display region P2 and the thumbnail display region P3. The control component 2, for example, darkens the display of the display region not associated with the thumbnail display region P3 as shown in FIG. 6.

Incidentally, the display feature for discriminating the presence from absence of association may be implemented by any method other than changing the brightness, such as changing the display color. In addition, it is also possible to identifiably display (such as displaying in the predetermined display color) the display region in which the image to be dragged is displayed (herein, the thumbnail display region P3).

Figure 7:
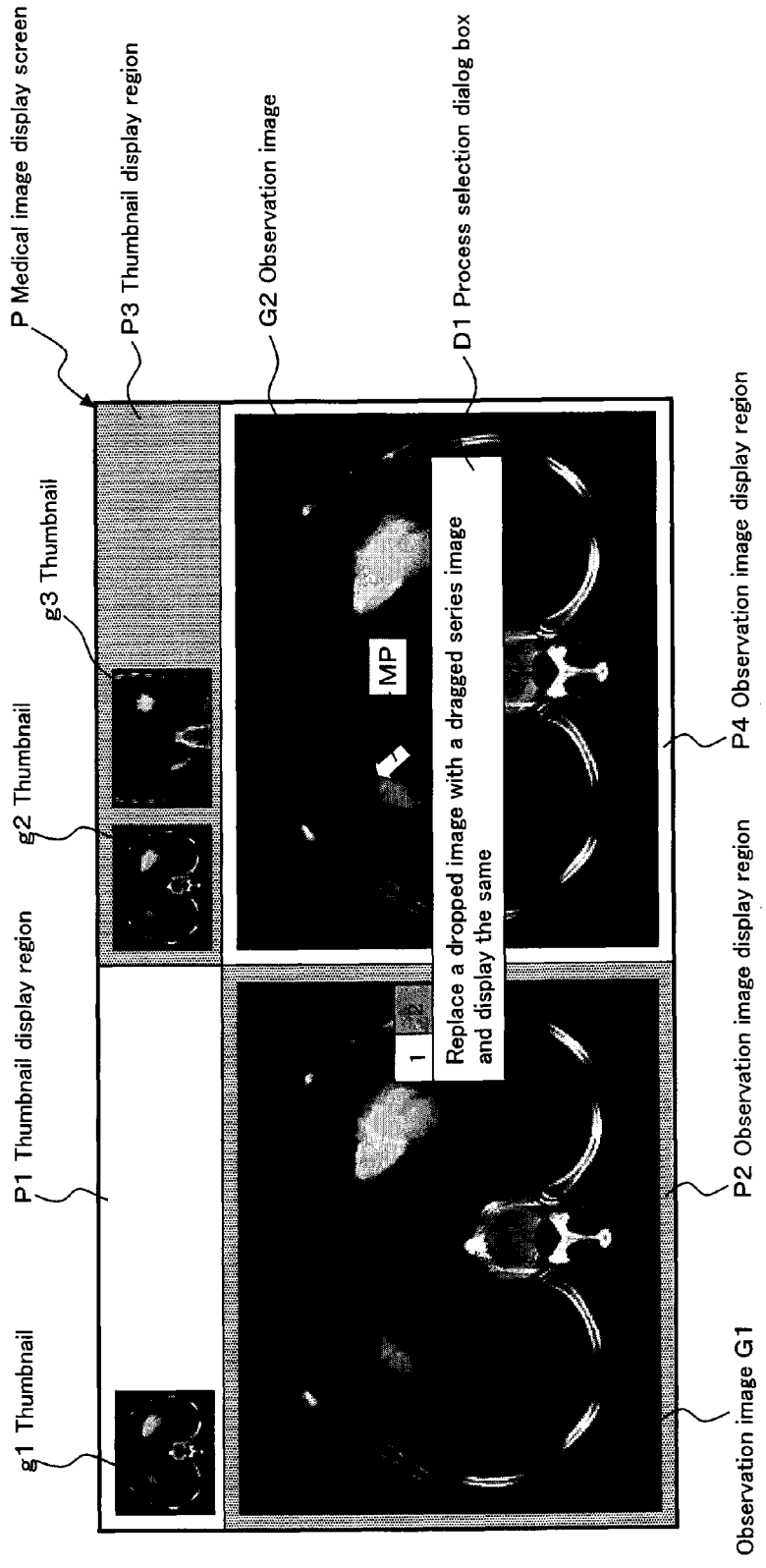
FIG. 7 is a diagram showing one example of display feature of the medical image display screen according to one embodiment of the medical image display apparatus according to the present invention.

When the thumbnail g3 is dragged to (the observation image G2 in) the observation image display region P4 (S13), the control component 2 instructs the display component 9 to display a process selection dialog box D1 as shown in FIG. 7 (S14). The process selection dialog box D1 selectably presents two items of the processing content associated with the combination of the thumbnail display region P3 and the observation image display region P4. Incidentally, the control component 2 recognizes the display region at the dragging destination, for example, based on the position of the mouse pointer MP on the display screen.

The process selection dialog box D1 is provided with tabs ("1" and "2" provided on the left top part of the process selection dialog box D1) for selecting one of the display image switch processing and the parallel display processing. The tabs are associated with the combination of the thumbnail display region P3 and the observation image display region P4.

The user alternately switches the processing indicated in the two tabs, for example, by rotating the mouse wheel (rotating part provided on the mouse). Then, the user selects one of either display image switch processing or parallel display processing, for example, by dropping the thumbnail g3 (S15).

Incidentally, this operation can be conducted by any method. For example, the process may be selected by clicking the desired tab or may be switched by pressing a predetermined key on the keyboard (such as a control key).

FIG. 7 shows a case in which tab "1" is selected. Tab "1" is associated to the display image switch processing. While tab "1" is selected, the explanation of the display image switch processing is displayed in the process selection dialog box D1 as follows: "Replace a dropped image with a dragged series image".

Figure 8:
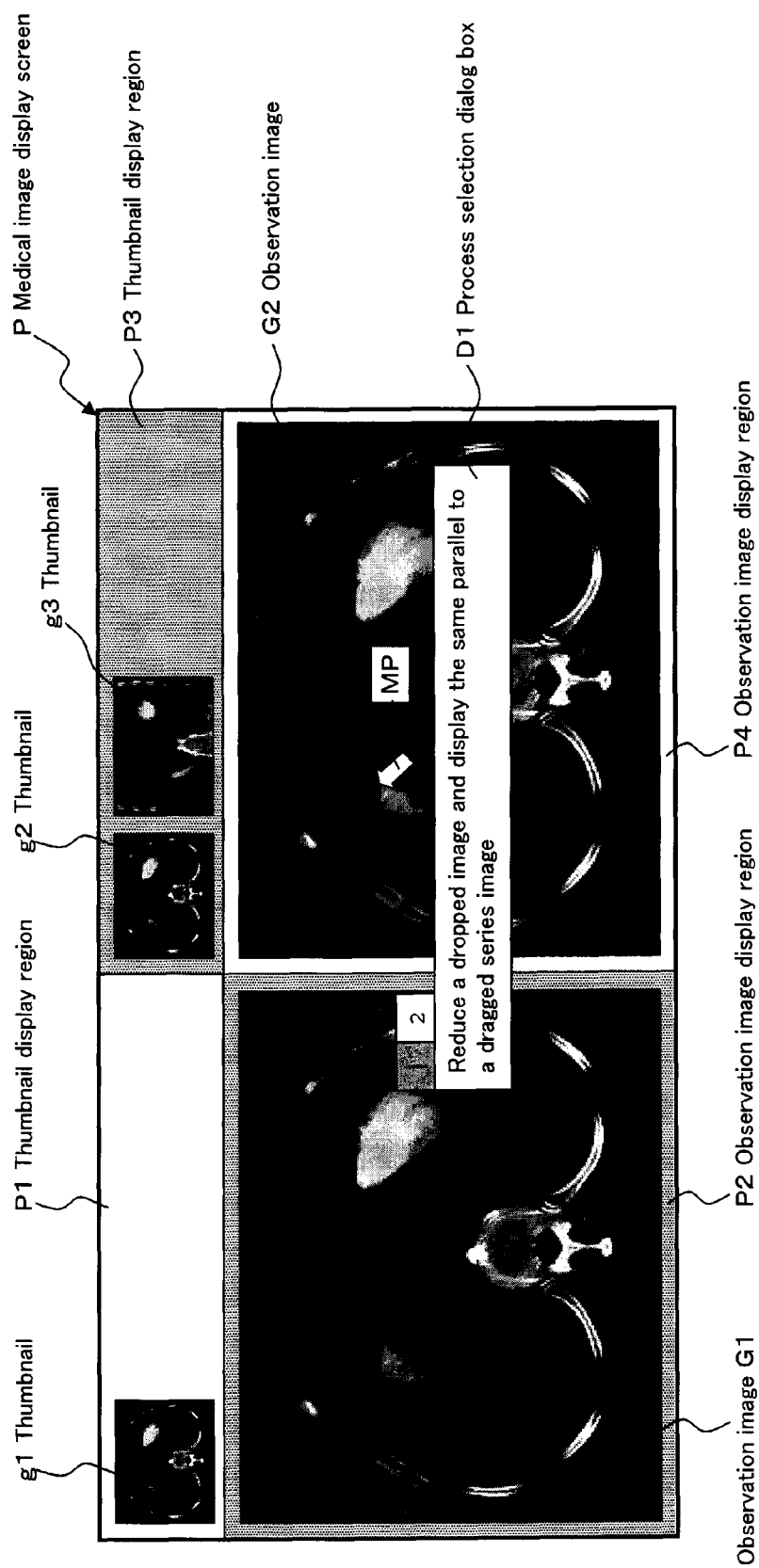
FIG. 8 is a diagram showing one example of display feature of the medical image display screen according to one embodiment of the medical image display apparatus according to the present invention.
Figure 9:
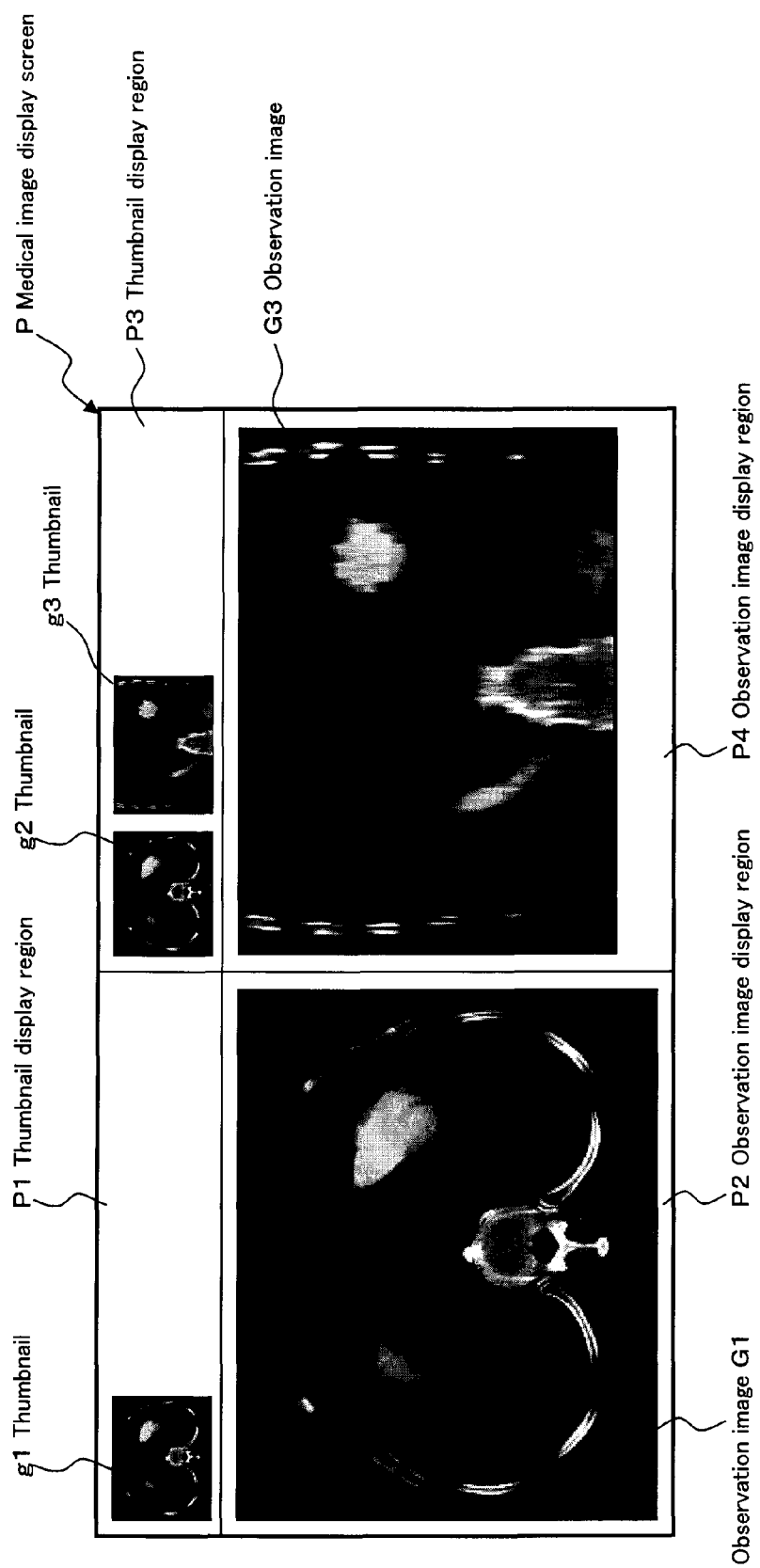
FIG. 9 is a diagram showing one example of display feature of the medical image display screen according to one embodiment of the medical image display apparatus according to the present invention.

In addition, FIG. 8 shows the state where tab "2" is selected. Tab "2" is associated to the parallel display processing. While tab "2" is selected, the explanation of the parallel display processing is displayed in the process selection dialog box D1 as follows: "Reduce a dropped image and display the same parallel to a dragged series image".

When the display image switch processing of tab "1" is selected (S16; image switching), the control component 2 will terminate the display of the observation image G2 displayed on the observation image display region P4. Furthermore, the control component 2 instructs to display the observation image G3 on the observation image display region P4 (S17). The observation image G3 is based on image data for medical images included in series corresponding to the thumbnail g3 (e.g. the medical image that has been first obtained among that series). As a result of instruction, the image displayed on the observation image display region P4 is switched from the observation image G2 to the observation image G3 as shown in FIG. 2.

Figure 10:
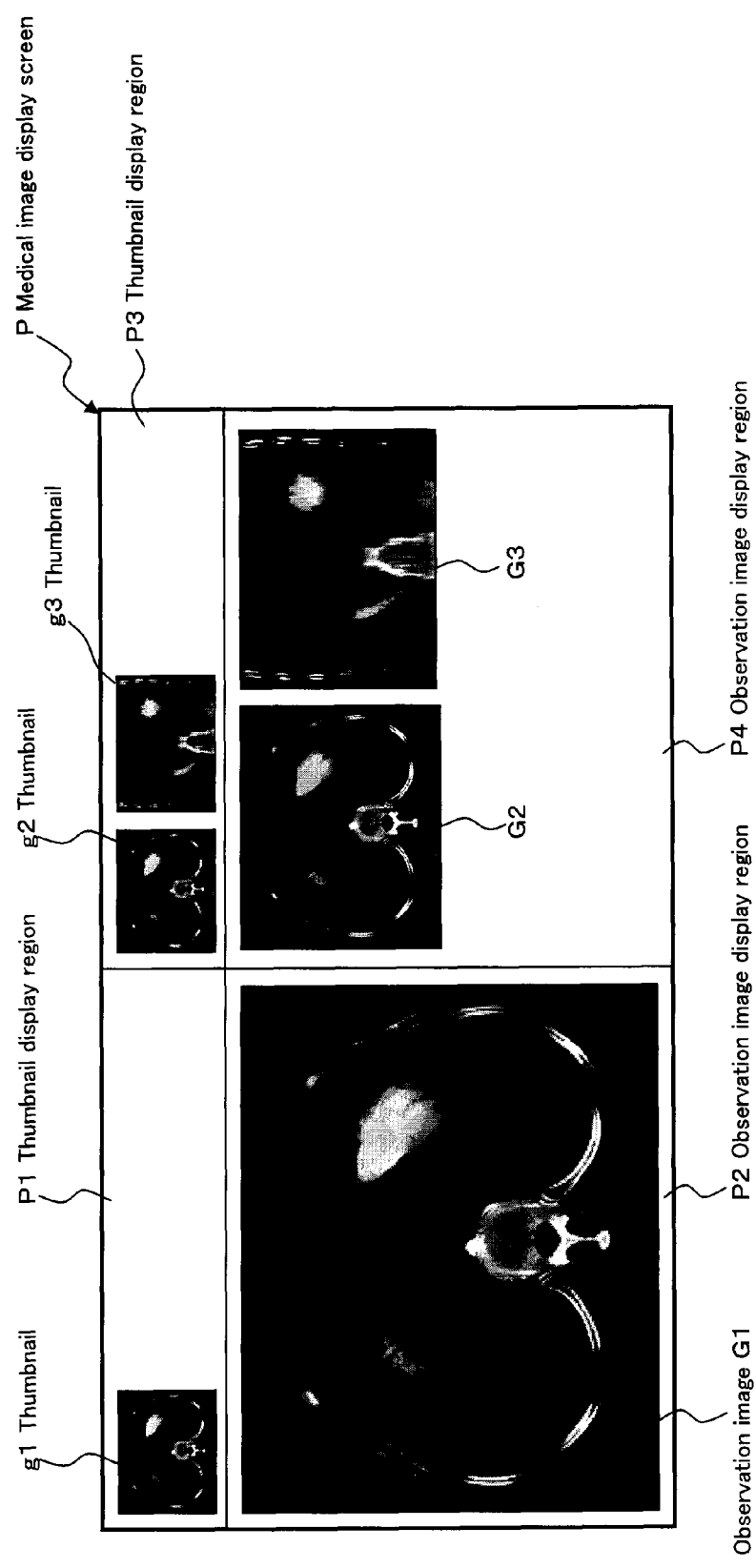
FIG. 10 is a diagram showing one example of display feature of the medical image display screen according to one embodiment of the medical image display apparatus according to the present invention.

On the other hand, when the parallel display processing of tab "2" is selected (S16; parallel display), the control component 2 will reduce the display size of the observation image G2 displayed on the observation image display region P4. Furthermore, the control component 2 instructs to display the observation image G3 side by side with the observation image g2 on the observation image display region P4 (S18). The observation image G3 is based on image data for medical images included in series corresponding to the thumbnail g3 (e.g. the medical image that has been first obtained among that series). As a result of instruction, the observation image G2 and the observation image G3 are displayed on parallel on the observation image display region P4 as shown in FIG. 10.

Incidentally, it is assumed that two or more thumbnails are displayed on the thumbnail display region P1 while the observation image corresponding to one of the thumbnails is displayed on the observation image display region P2. In this case, when dragging and dropping another thumbnail onto (the observation image displayed on) the observation image display region P2, processing similar to the above processing illustrated in FIG. 5 to FIG. 10 is performed.

Figure 11:
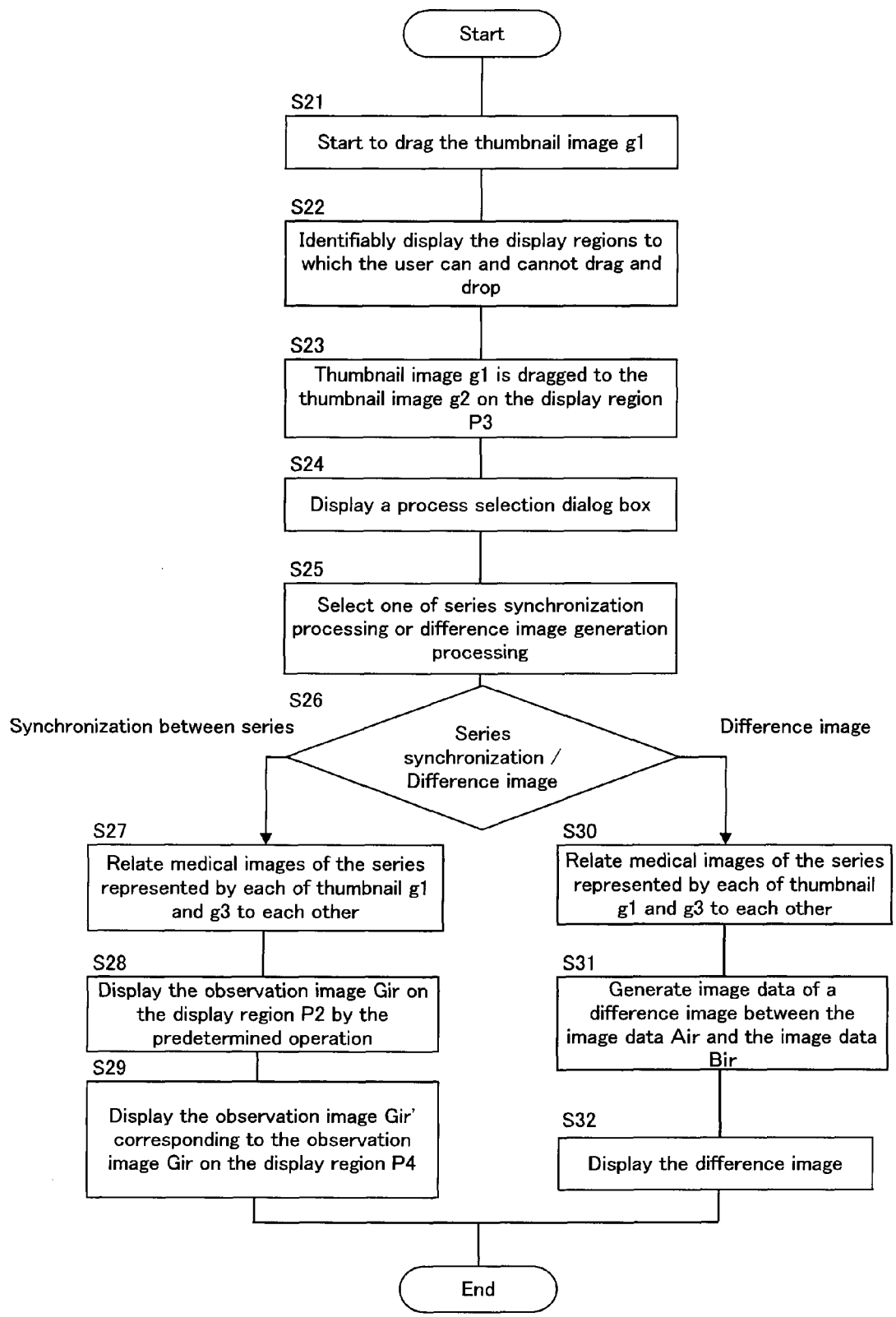
FIG. 11 is a flow chart showing one example of processing performed by one embodiment of the medical image display apparatus according to the present invention.

Synchronization Between Series Processing and Difference Image Generating Processing Next, the synchronization between series processing and the difference image generating processing are described with reference to the flow chart of FIG. 11. These processing will be performed, as shown in FIG. 3, when dragging and dropping the thumbnail displayed on the thumbnail display region P1 onto (the thumbnail displayed on) the thumbnail display region P3 or when dragging and dropping the thumbnail displayed on the thumbnail display region P3 on (the thumbnail displayed on) the thumbnail display region P1.

Herein, a case in which the thumbnail g1 on the thumbnail display region P1 is dragged and dropped on the thumbnail g2 displayed on the thumbnail display region P3 in the display state shown in FIG. 4 is described. Incidentally, the illustration of the mouse pointer MP will be omitted hereinafter.

First, the user points the mouse pointer MP on the thumbnail g1 by operating the mouse of the operation component 10 and starts to drag the thumbnail g1 onto the medical image display screen P shown in FIG. 4 (S21). The control component 2 instructs to display the display region associated with the thumbnail display region P1 on which the thumbnail g1 is displayed and the display region not associated with the same in identifiable display feature respectively with reference to the process associating information 32a (S22).

In the present embodiment, the display regions associated with the thumbnail display region P1 are the observation image display region P2, the thumbnail display region P3, and the observation image display region P4. The control component 2 instructs to darken the display of only the thumbnail display region P1 itself (illustration is omitted).

When the thumbnail g1 is dragged to (the thumbnail g2 on) the thumbnail display region P3 (S23), the control component 2 instructs the display component 9 to display a process selection dialog box D2 (S24). The process selection dialog box D2 selectably presents the synchronization between series processing and the difference image generating processing associated with the combination of the thumbnail display region P1 and the thumbnail display region P3.

Although the illustration is omitted, the process selection dialog box D2 is provided with tabs for selecting one of the synchronization between series processing and the difference image generating processing similar to the process selection dialog box D1 of FIG. 7 and FIG. 8. When tabs is switched with a mouse, the explanation of the synchronization between series processing according to tab "1" and the explanation of the difference image generating processing according to tab "2" are switched to display. The explanation according to tab "1" is as follows: "perform the synchronization between series functions of two series, i.e. the series from which and to which the image was dragged and dropped". The explanation according to tab "2" as follows: "create the time-series difference image between the image from which and to which the image was dragged and dropped". The user selects one processing of the synchronization between series processing and the difference image generating processing by the process selection dialog box D2 (S25).

When the synchronization between series processing of tab "1" is selected (S26; synchronization between series), the medical image associating component 7 associates medical images included in a series of medical images represented by the thumbnail g1 with medical images included in a series of medical images represented by the thumbnail g3 based on the incidental information (S27).

This association will now be more specifically described. Now assume that image data for a series of medical images represented by the thumbnail g1 is series A of FIG. 2 and image data for a series of medical images represented by the thumbnail g2 is series B. The medical image associating component 7 associates the image data A1 to Am from series A with the image data B1 to Bn from series B. For this purpose, the incidental information a1 to am and the incidental information b1 to bn are referred.

Image position information (described above) indicating the position of the medical image is recorded on each incidental information a1 to am and b1 to bn. The medical image associating component 7 associates the image data Ai (i=1 to m) with the image data Bj (j=1 to n) in which the image positions indicated in the image position information are almost identical. Particularly, when the thumbnails g1 and g3 are tomographic images, the medical image associating component 7 associates image data in which the cross-sectional position indicated in the cross-sectional position information and the cross-sectional direction indicated in the cross-sectional direction information are almost identical.

Assume that the image data Ai1 and the image data Bj1 are associated with each other, the image data Ai2 and the image data Bj2 are associated with each other, . . . , and the image data Ajk and the image data Bjk are each associated in this way.

The user operates the operation component 10 to display the observation image Gir based on the image data Air (r=1 to k) on the observation image display region P2 (S28). The control component 2 instructs to display the observation image Gir' based on the image data Bir associated with the image data Air on the observation image display region P4, with reference to the results of the above associating processing (S29). On the contrary, when the user operates to display the observation image Gir' based on the image data Bir on the observation image display region P4, the control component 2 instructs to display the observation image Gir based on the image data Air associated with the image data Bir on the observation image display region P2.

In this way, in the synchronization with one observation image having been switched, another observation image will be automatically switching displayed. Furthermore, two observation images displayed in synchronization are the medical images in which the image positions are almost identical.

On the other hand, the difference image generating processing of tab "2" is selected (S26; difference image), the medical image associating component 7 performs the association processing similar to the above (S30). The difference image generating component 5 generates image data for the difference image of the associated image data Air and image data Bir (S31). The control component 2 instructs the display component 9 to display this difference image, automatically or in response to a user request (S32). This difference image is displayed, for example, on the observation image display region P2. Incidentally, image data for k number of difference images are generated at step S31. The control component 2 sequentially instructs to display these k difference images, for example, based on operation by the operation component 10.

Incidentally, when dragging and dropping a thumbnail displayed on the thumbnail display image P3 on a thumbnail displayed on the thumbnail display region P1, processing similar to the above is performed.

In addition, the synchronization between series processing and the difference image generating processing are each performed only between series in which these processing can be performed. That is, the synchronization between series processing is performed only in the case where the image positions of each series can be associated. For example, the synchronization between series processing can be performed between series in which the cross-sectional directions are identical, but cannot performed between series in which the cross-sectional directions are different. Similarly, the difference image generating processing can be performed only between series in which the difference image can be defined. At step S22, it may be designed to identifiably display thumbnails capable of performing the synchronization between series processing or the difference image generating processing and thumbnails incapable of such.

In the above example, image position information for incidental information associates almost identical medical images with each other, but is not limited to this. For example, it is also possible to associate medical images in which the imaging phase indicated in the imaging phase information are almost identical, so as to perform the synchronization between series processing or the difference image generating processing. Such configuration is effective for the series of medical images representing a time change at the site to be obtained such as by ECG gated scan.

For example, when series A and B represented by the thumbnails g1 and g3 each consist of a plurality of medical images obtained by the ECG gated scan, it is possible to associate with medical images in which the imaging phases are almost identical. Furthermore, it is possible to display associated medical images in synchronization and to generate image data for the difference image between the associated medical images.

Tomographic Image Generation Processing

Figure 12:
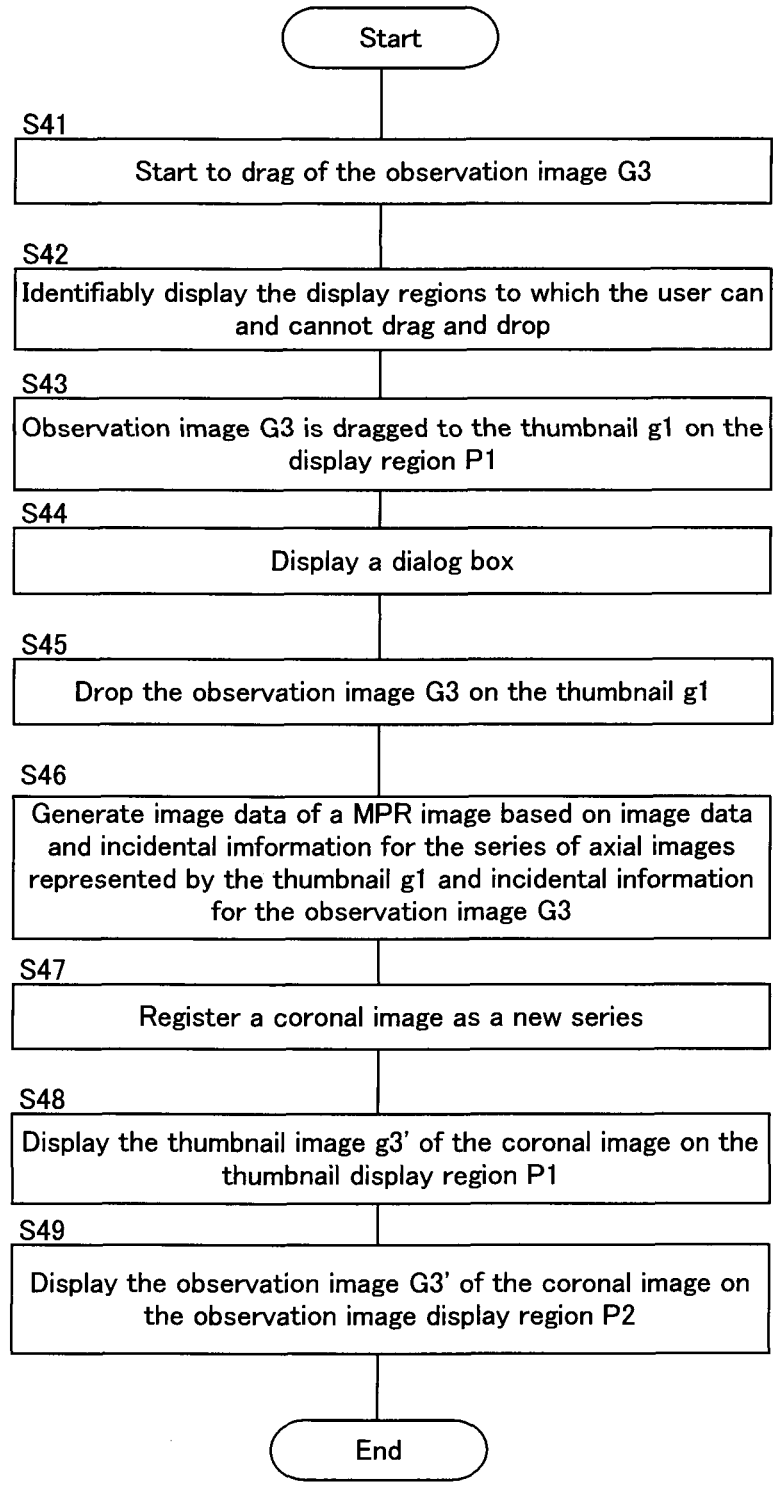
FIG. 12 is a flow chart showing one example of processing performed by one embodiment of the medical image display apparatus according to the present invention.
Figure 13:
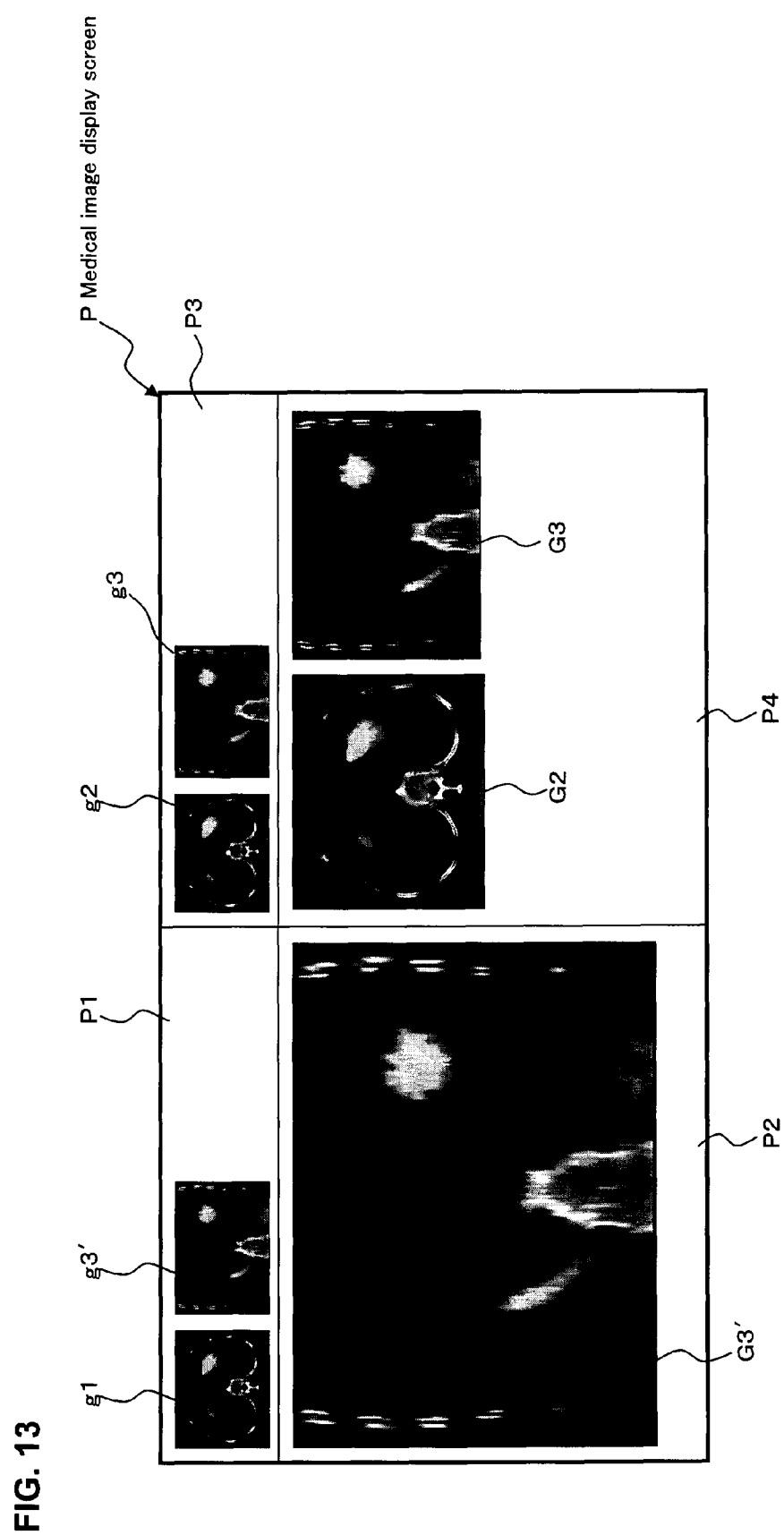
FIG. 13 is a diagram showing one example of display feature of the medical image display screen according to one embodiment of the medical image display apparatus according to the present invention.

Next, the tomographic image generation processing is described with reference to FIG. 12 and FIG. 13. The tomographic image generation processing is performed as shown in FIG. 3 at the time as follows: (1) after having dragged and dropped the thumbnail displayed on the thumbnail display region P1 on (the observation image displayed on) the observation image display region P4; or (2) after having dragged and dropped the observation image displayed on the observation image display region P4 on (the thumbnail displayed on) the thumbnail display region P1.

Herein, a case of dragging and dropping in the display state shown in FIG. 10 is described, wherein the observation image G3 displayed on the observation image display region P4 is dragged and dropped on the thumbnail g1 on the thumbnail display region P1. Incidentally, the observation image G3 is an image based on image data of a coronal image generated by applying multiplanar reformation (MPR) to image data of a series of axial images represented by the thumbnail g2 (one of them is the observation image G2). In addition, a series of medical images represented by the thumbnail g1 are axial images of the same cross-sectional direction as the thumbnail g2.

First, the user points the mouse pointer MP on the observation image G3 by operating the mouse of the operation component 10 and starts to drag the observation image G3 on the medical image display screen P shown in FIG. 10 (S41). The control component 2 instructs to display the display region associated with the observation image display region P4 on which the observation image G3 is displayed and the display region not associated with the same in each identifiable display feature with reference to the process associating information 32a (S42).

In the present embodiment, the display regions associated with the observation image display region P4 are thumbnail display region P1 and observation image display region P2. The control component 2 darkens the display of the thumbnail display region P3 and the observation image display region P4 (illustration is omitted).

When the observation image G3 is dragged to (the thumbnail g1 of) the thumbnail display region P1 (S43), the control component 2 instructs the display component 9 to display a dialog box D3 (S44). The dialog box D3 presents the explanation of processing content of the tomographic image generation processing associated with the combination of the observation image display region P4 and the thumbnail display region P1, "create MPR images from the series to which to drag and drop in the same condition as the MPR images from which to drag and drop series, and register them as a new series."

Herein, according to the process associating information 32a of FIG. 3, processing associated with the combination of the observation image display region P4 and the thumbnail display region P1 are three, i.e. the tomographic image generation processing; the approximate section image selection processing; and the fusion image generation processing. Among them, the tomographic image generation processing is performed when medical images from which to drag and drop and medical images to which to drag and drop have different cross-sectional directions. On the other hand, the rest of the processing is performed when medical images from which to drag and drop and medical images to which to drag and drop have the same cross-sectional direction. At step S44, the control component 2 recognizes that the cross-sectional direction of a medical image from which to drag and drop (observation image G3) and the cross-sectional direction of a medical image to which to drag and drop (thumbnail g1) are different with reference to their incidental information, and instructs to display a dialog box D3 related to the tomographic image generation processing. Incidentally, dialog boxes related to the latter two processing will be described later.

The user operates the operation component 10 by dropping the observation G3 on the thumbnail g1 in order to require performing the tomographic image generation processing (S45). The tomographic image generating component 6 performs MPR processing based on image data of a series of medical images represented by the thumbnail g1 (axial images), incidental information (cross-sectional position information, cross-sectional direction information) of this image data, and incidental information (cross-sectional position information, cross-sectional direction information) of the observation image G3 (coronal image), and thereby generates image data of the MPR image (coronal image) of this series of axial images (S46).

The control component 2 stores image data (and the incidental information) of the generated coronal image in the image data storage component 32 and registers it as a new series (S47). The thumbnail generating component 4 generates image data of the thumbnail g3' of this coronal image. The control component 2 instructs to display this thumbnail g3' on the thumbnail display region P1 (S48). The control component 2 instructs to display the observation image G3' of this coronal image on the observation image display region P2 automatically or in response to a user request as shown in FIG. 13 (S49).

Incidentally, procedure to obtain a coronal image from an axial image is described in the above example, but it is also possible to obtain another image from one image of an axial image, a coronal image, and a sagittal image. In addition, it is also possible to obtain an oblique image of any cross-sectional direction based on a series of medical images of any cross-sectional direction.

Approximate Section Image Selection Processing and Fusion Image Generation Processing Next, the approximate section image selection and the fusion image generation are described with reference to FIG. 14. These processings are performed when the thumbnail displayed on the thumbnail display region P1 has been dragged and dropped on (the observation image of) the observation image display region P4 or when the observation image displayed on the observation image display region P4 has been dragged and dropped on (the thumbnail displayed on) the thumbnail display region P1 as shown in FIG. 3.

Herein, procedure in the display state shown in FIG. 10 to drag and drop the observation image G2 on the thumbnail g1 on the thumbnail display region P1 is described, the observation image G2 being displayed on the observation image display region P4. The observation image G2 is an observation image of a series of axial images represented by the thumbnail g2. In addition, the thumbnail g1 is a thumbnail of axial images of the same cross-sectional direction as the thumbnail g2. Particularly, tomographic images represented by the thumbnail g1 and the observation image G2 are sufficient to be tomographic images of the same cross-sectional direction. It is determined by cross-sectional direction information whether the cross-sectional directions are the same. Their tomographic images of the same cross-sectional direction may be tomographic images obtained by each different modality, or may be tomographic images obtained by a different examination method.

First, on the medical image display screen P shown in FIG. 10, the user points the mouse pointer MP on the observation image G2 and starts to drag the observation image G2 (S51). The control component 2 darkens the display of the thumbnail display region P3 and the observation image display region P4 not associated with the observation image display region P4 on which the observation image G2 is displayed with reference to the process associating information 32a (S52).

When the observation image G2 is dragged to (the thumbnail g1 of) the thumbnail display region P1 (S53), the control component 2 instructs the display component 9 to display a process selection dialog box D4 (S54). The process selection dialog box D4 selectably presents the approximate section image selection processing and the fusion image generation processing associated with the combination of the observation image display region P4 and the thumbnail display region P1.

Although the illustration is omitted, as similar to the process selection dialog box D1 of FIG. 7 and FIG. 8, the process selection dialog box D4 is provided with tabs for selecting one of the approximate section image selection processing and the fusion image generation processing. When the tabs are switched with the mouse, the explanation of the approximate section image selection processing corresponding to the tab "1" and the explanation of the fusion image generation processing corresponding to the tab "2" are switched for display. The explanation corresponding to the tab "1" is as follows: "display the image to which to drag and drop with the coordinates close to the image from which to drag and drop". The explanation corresponding to the tab "2" as follows: "create a fusion image with the same coordinates as the image from which to drag and drop". The user selects the approximate section image selection processing or the fusion image generation processing by the process selection dialog box D4 (S55).

When the approximate section image selection processing of tab "1" is selected (S56; approximate section), the control component 2 selects, a tomographic image having the cross-sectional position that is almost identical to the observation image G2 (cross-sectional position that is the closest to the observation image G2) from the following series of tomographic images. This selection is based on incidental information (cross-sectional position information) of the observation image G2 (axial image) and the incidental information (cross-sectional position information) of each of the tomographic images (axial images) of the series represented by the thumbnail g1. Furthermore, the control component 2 instructs to display the selected tomographic image on the observation image display region P2 (S57). The selection processing of tomographic images can be easily performed by searching for the one closest to the cross-sectional position of the observation image G2 among the cross-sectional position information of the series of tomographic images.

On the other hand, when the fusion image generation processing of the tab "2" is selected (S56; fusion), the control component 2 selects a tomographic image having the cross-sectional position that is almost identical to the observation image G2 (cross-sectional position closest to the observation image G2) from the following series of tomographic images (S58). This selection is based on the cross-sectional position information corresponding to the observation image G2 and the cross-sectional position information of each of the tomographic images of the series represented by the thumbnail g1. Furthermore, the control component 2 adjusts the position between the selected tomographic image and the observation image G2 by controlling the image position adjusting component 8 (S59). This processing is performed, for example, by adjusting the coordinates indicated in the image position information of the selected tomographic image to the coordinates indicated in the image position information of the observation image G2. In addition, it is also possible to conduct position adjustment by matching the positions of characteristic sites of each image.

The control component 2 instructs the display component 9 to display a fusion image consisting of the position-adjusted tomographic image and the observation image G2 (S60).

While a fusion image consisting of two tomographic images are generated in the above example, it is also possible to generate a fusion image including a pseudo three-dimensional image based on the volume data. Herein, the pseudo three-dimensional is an image obtained by rendering processing such as volume rendering and MIP (Maximum Intensity Projection). In addition, the number of medical images composing a fusion image is not limited to two, but may be three or more.

Annotation Attachment Processing and Measurement Attachment Processing

Figure 15:
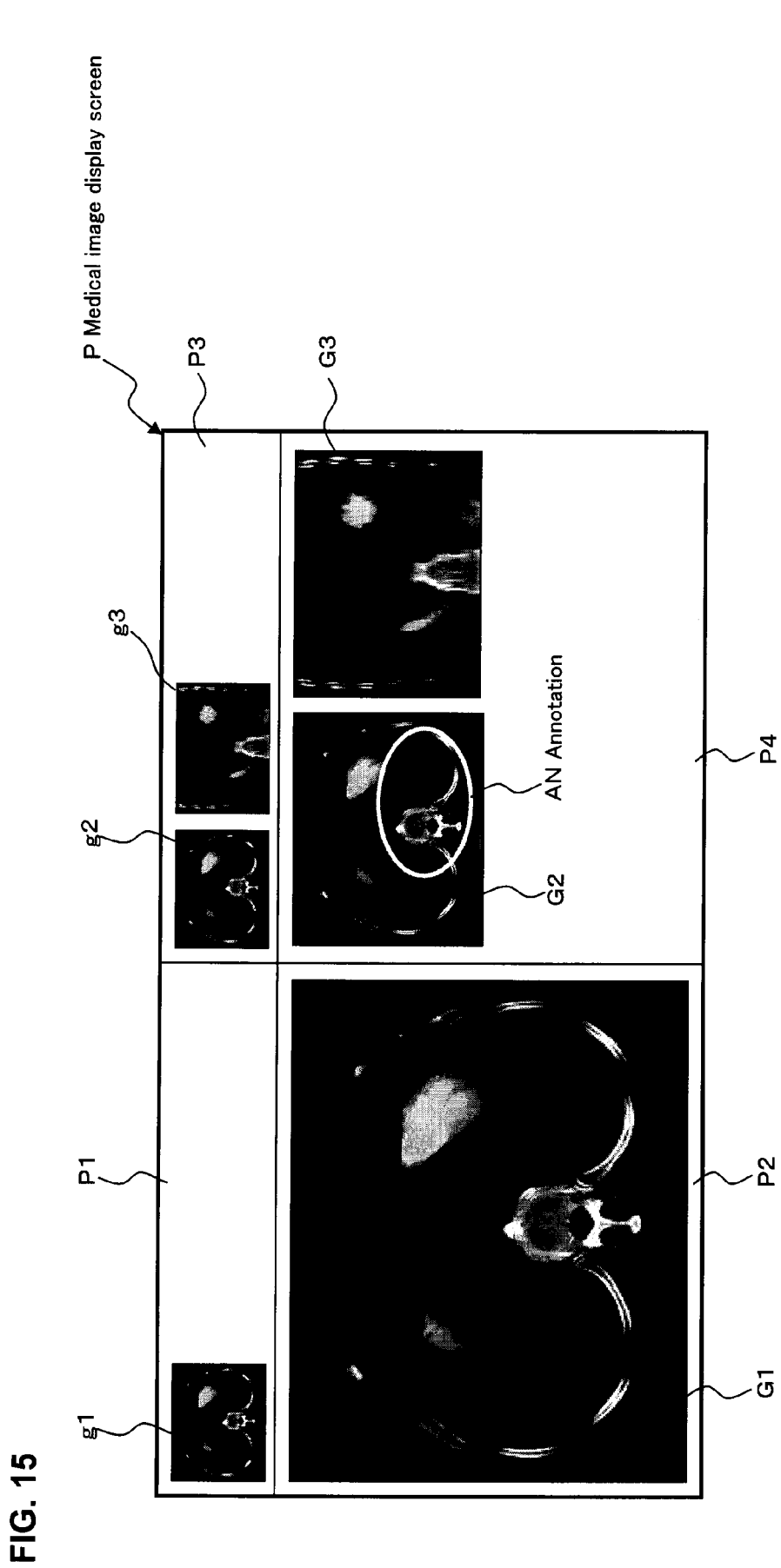
FIG. 15 is a diagram showing one example of display feature of the medical image display screen according to one embodiment of the medical image display apparatus according to the present invention.
Figure 16:
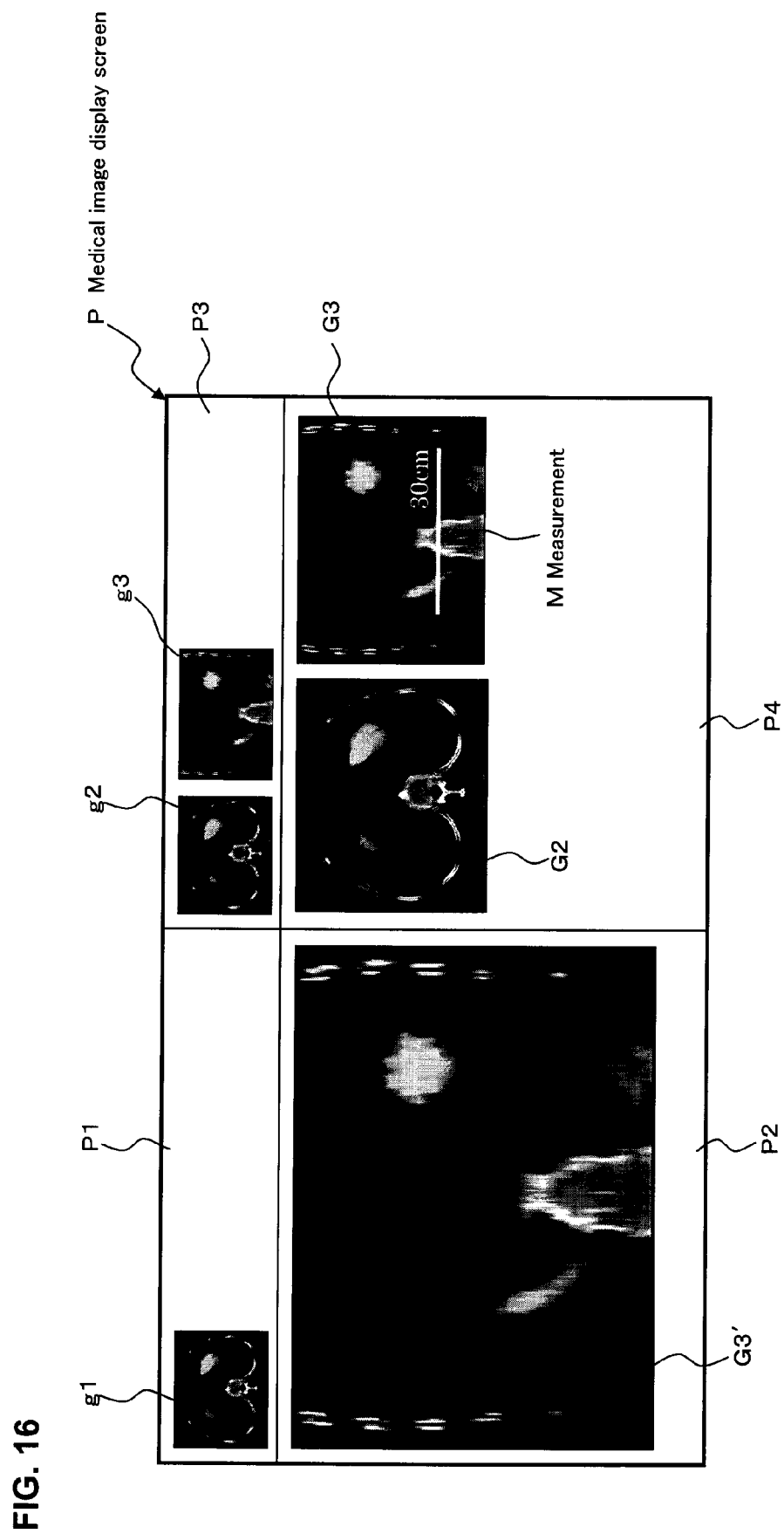
FIG. 16 is a diagram showing one example of display feature of the medical image display screen according to one embodiment of the medical image display apparatus according to the present invention.

Next, the annotation attachment processing and the measurement attachment processing are described with reference to FIG. 15 to FIG. 20. FIG. 15 and FIG. 16 each show one example of annotation (annotation image) and measurements (measured image) attached to a medical image.

The annotation AN shown in FIG. 15 consists of oval images attached to the noted site of the observation image G2. The annotation AN will be displayed based on the annotation information (described above) recorded in incidental information of the observation image G2 when the user conducts the predetermined operation.

In addition, the measurement M shown in FIG. 16 is an image indicating the measurement of the distance in the observation image G3. The measurement M includes a linear image indicating the measured site and the image of the numeric value "30 cm" indicating the measured distance. Incidentally, the observation image G3' of the coronal image shown in FIG. 13 is displayed on the observation image display region P2 of FIG. 16.

The annotation attachment processing and the measurement attachment processing are performed when annotation or measurement displayed on the observation image display region P4 has been dragged and dropped on (the observation image displayed on) the observation image display region P2 as shown in FIG. 3. Incidentally, it is also possible to perform the annotation attachment processing or the measurement attachment processing by dragging and dropping an observation image attached by annotation or measurement.

Annotation Attachment Processing

Figure 17:
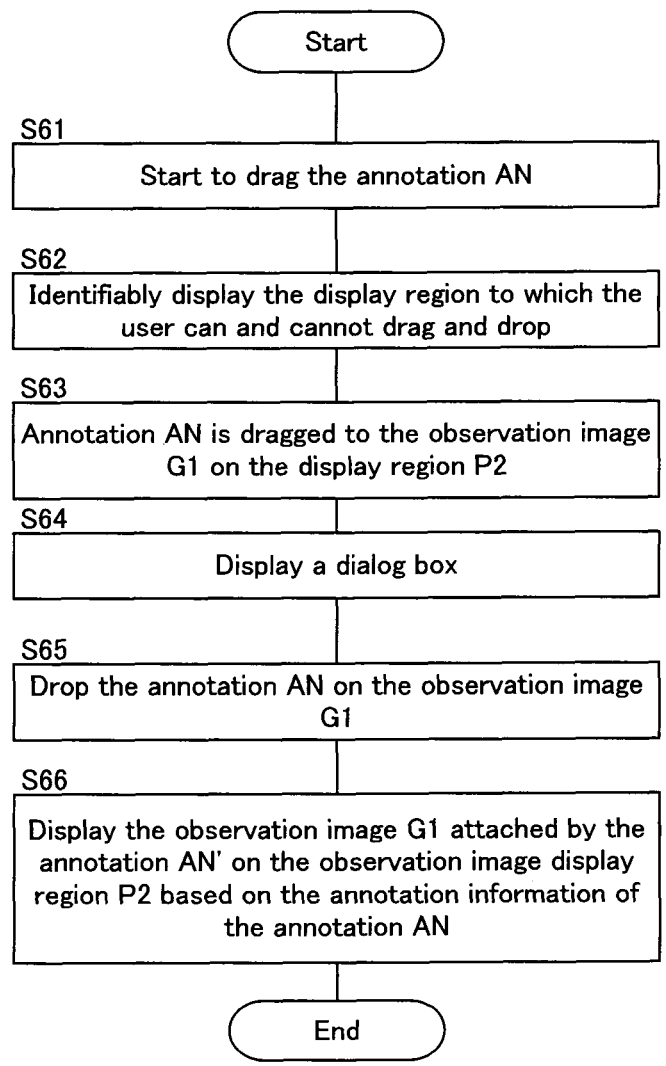
FIG. 17 is a flow chart showing one example of processing performed by one embodiment of the medical image display apparatus according to the present invention.
Figure 18:
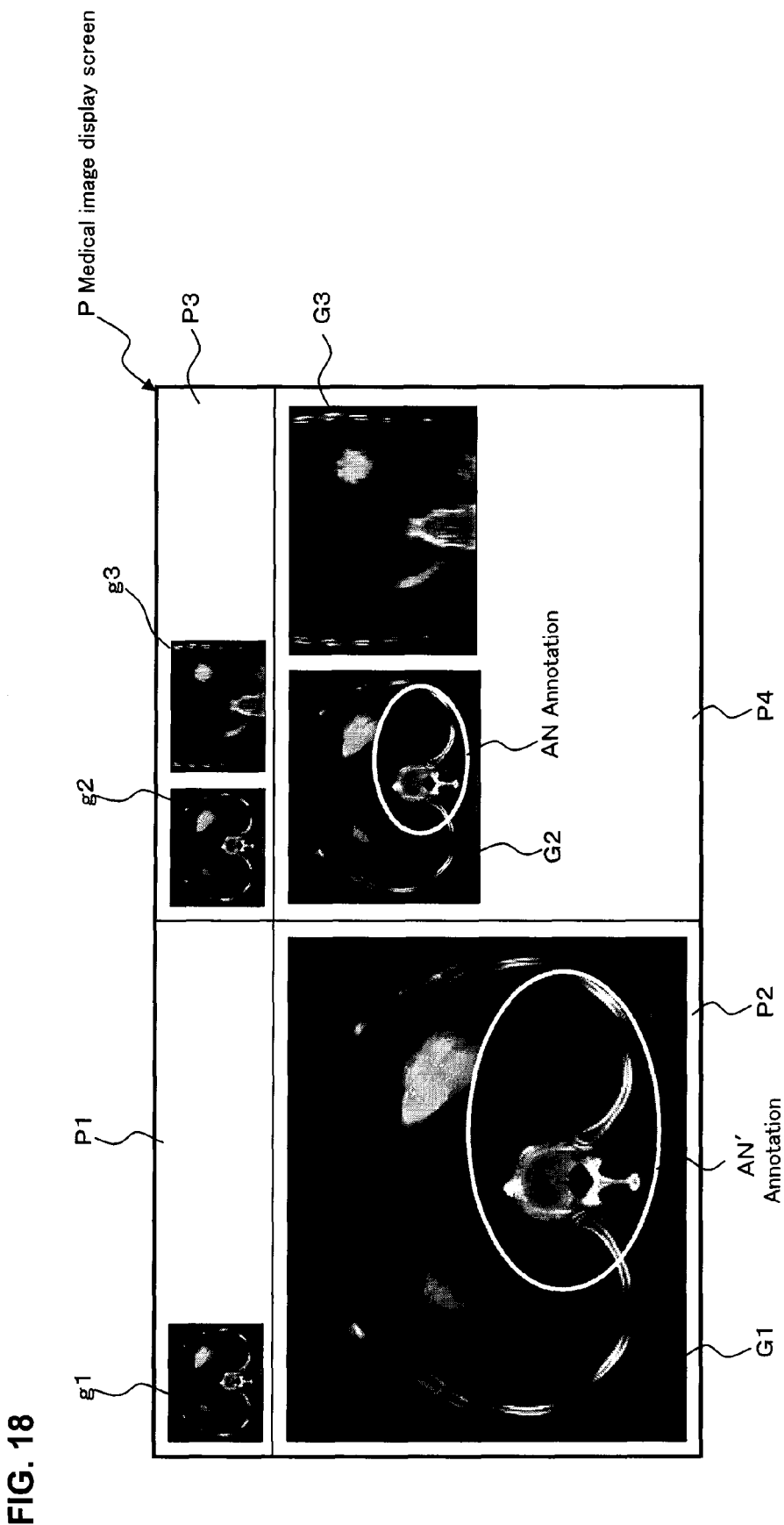
FIG. 18 is a diagram showing one example of display feature of the medical image display screen according to one embodiment of the medical image display apparatus according to the present invention.

The annotation attachment processing is described with reference to FIG. 17 and FIG. 18. First, the mouse pointer MP is disposed on the annotation AN (or the observation image G2; hereinafter same as above) on the medical image display screen P shown in FIG. 15. When dragging of the annotation AN starts (S61), the control component 2 darkens the display of the thumbnail display region P3 and the observation image display region P4 not associated with the observation image display region P4 in which the annotation AN is displayed with reference to the process associating information 32a (S62).

When the annotation AN is dragged to (the observation image G1 of) the observation image display region P2 (S63), the control component 2 instructs the display component 9 to display a dialog box D5 (S64). The dialog box D5 presents the explanation of the processing content of the annotation attachment processing associated with the combination of the observation image display region P4 and the observation image display region P2 as follows: "display the same form of annotation as the image from which to drag and drop at the same coordinates on the image to which to drag and drop." Incidentally, the control component 2 recognizes that the image being dragged is an annotation with reference to incidental information of the observation image G2.

The user operates the operation component 10 and drops the annotation AN on the observation image G1 in order to require to perform the annotation attachment processing (S65). The control component 2 having received this request instructs to display the observation image G1 attached by the annotation AN' on the observation image display region P2 as shown in FIG. 18 based on annotation information regarding the annotation AN (S66). The annotation AN' represents the display position and display size corresponding to the annotation AN.

At this time, it is possible to display the annotation AN' overlapping over the observation image G1 having been already displayed. In addition, it is also possible to generate a new image data in which image data of the annotation AN' is overlapped on image data of the observation image G1 and to display an objective image based on this new image data.

In addition, the control component 2 determines the position where the annotation AN' is overlapping the observation image G1 and the display size (enlargement magnification ratio/reduction magnification ratio) of the annotation AN based on the coordinates indicated in the image position information of the observation image G1 and information regarding the position and size of the annotation AN indicated in the annotation information.

It is constituted so as to, in response to the annotation AN having been dragged and dropped onto the observation image G1, display the similar annotation AN' attached to the observation image G1 in the above example, but other configurations can be also applied. For example, it is possible to automatically shift to the mode for entering annotations to the observation image G1 (annotation entering mode) in response to the similar operation. That is, it is possible to automatically activate the computer program for entering annotations in response to that operation. As for the method of entering annotations in the annotation entering mode, for example, any conventional method can be used.

Although the annotation in the above example is a two-dimensional image, it is also possible to display, for example, an annotation consisting of a three-dimensional image. At this time, the observation image is, for example, a pseudo three-dimensional image based on volume data. In addition, when attaching an annotation to an observation image of a tomographic image based on volume data, an image of a cross-section of a three-dimensional annotation at the cross-sectional position of this tomographic image can be displayed attached to an observation image of this tomographic image.

Measurement Attachment Processing

Figure 19:
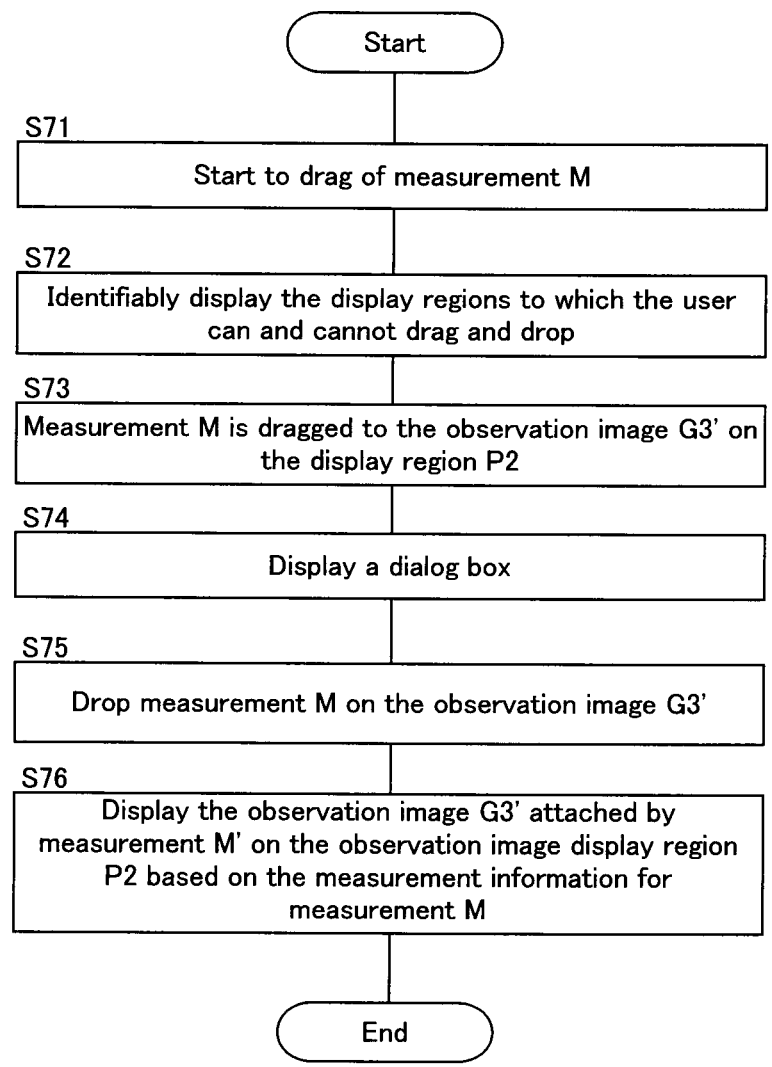
FIG. 19 is a flow chart showing one example of processing performed by one embodiment of the medical image display apparatus according to the present invention.
Figure 20:
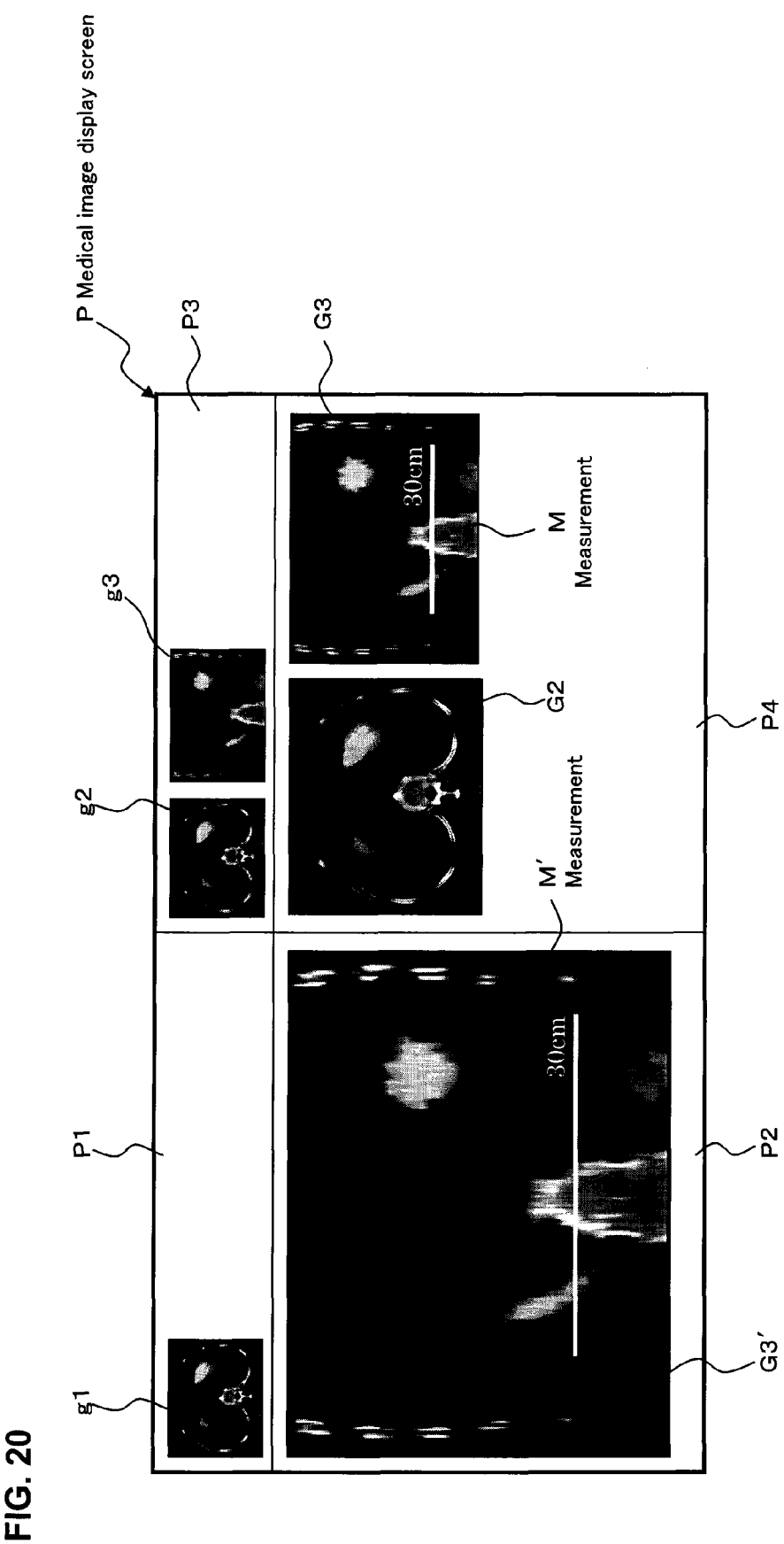
FIG. 20 is a diagram showing one example of display feature of the medical image display screen according to one embodiment of the medical image display apparatus according to the present invention.

The measurement attaching process is described with reference to FIG. 19 and FIG. 20. First, a mouse pointer MP is disposed on the measurement M (or the observation image G3; hereinafter same as above) on the medical image display screen P shown in FIG. 19. When the drag of the measurement M starts (S71), the control component 2 darkens the display of the thumbnail display region P3 and the observation image display region P4 not associated with the observation image display region P4 in which the measurement M is displayed with reference to the process associating information 32a (S72).

When the measurement M is dragged to (the observation image G3' of) the observation image display region P2 (S73), the control component 2 instructs the display component 9 to display a dialog box D6 (S74). The dialog box D6 presents the explanation of the processing content the measurement attachment processing associated with the combination of the observation image display region P4 and the observation image display region P2 as follows: "display the same dimension of measurement as the image from which to drag and drop at the same coordinates on the image to which to drag and drop." Incidentally, the control component 2 recognizes that the image being dragged is the result of measurement by reference to the incidental information belonging to the observation image G3.

The user operates the operation component 10 and drops the measurement M on the observation image G3' in order to require to perform the measurement attachment processing (S75). The control component 2 having received this request instructs to display the observation image G3' attached by the measurement M' which display position and display size correspond to the measurement M on the observation image display region P2 as shown in FIG. 20 based on the measurement information of measurement M (S76).

At this time, it is also possible to display the measurement M' overlapping the observation image G3' already displayed. In addition, it is also possible to generate a new image data in which image data of the measurement M overlaps with image data of the observation image G3' and to perform the display processing based on this new image data.

In addition, the control component 2 determines the position where the measurement M' is overlapping the observation image G3' and the display size (enlargement magnification ratio/reduction magnification ratio) based on the coordinates indicated in the image position information of the observation image G3' and information regarding the position and size of the measurement M indicated in the measurement information.

In the above example, in response to the measurement M having been dragged and dropped onto the observation image G3', the measurement M' attached to the observation image G3' is displayed, but other configuration can be also applied. For example, it is possible to automatically shift to the mode for plotting the measurement for the observation image G3' (measurement plotting mode) in response to a similar operation. That is, it is possible to automatically activate the computer program for plotting the measurement in response to said operation. As for the method of plotting measurement, for example, any conventional method can be used.

In the above example, the measurement attachment processing between tomographic images having the same cross-sectional position is described, while it is possible to perform the measurement attachment processing also between tomographic images in which the cross-sectional positions or the cross-sectional directions are different.

Figure 14:
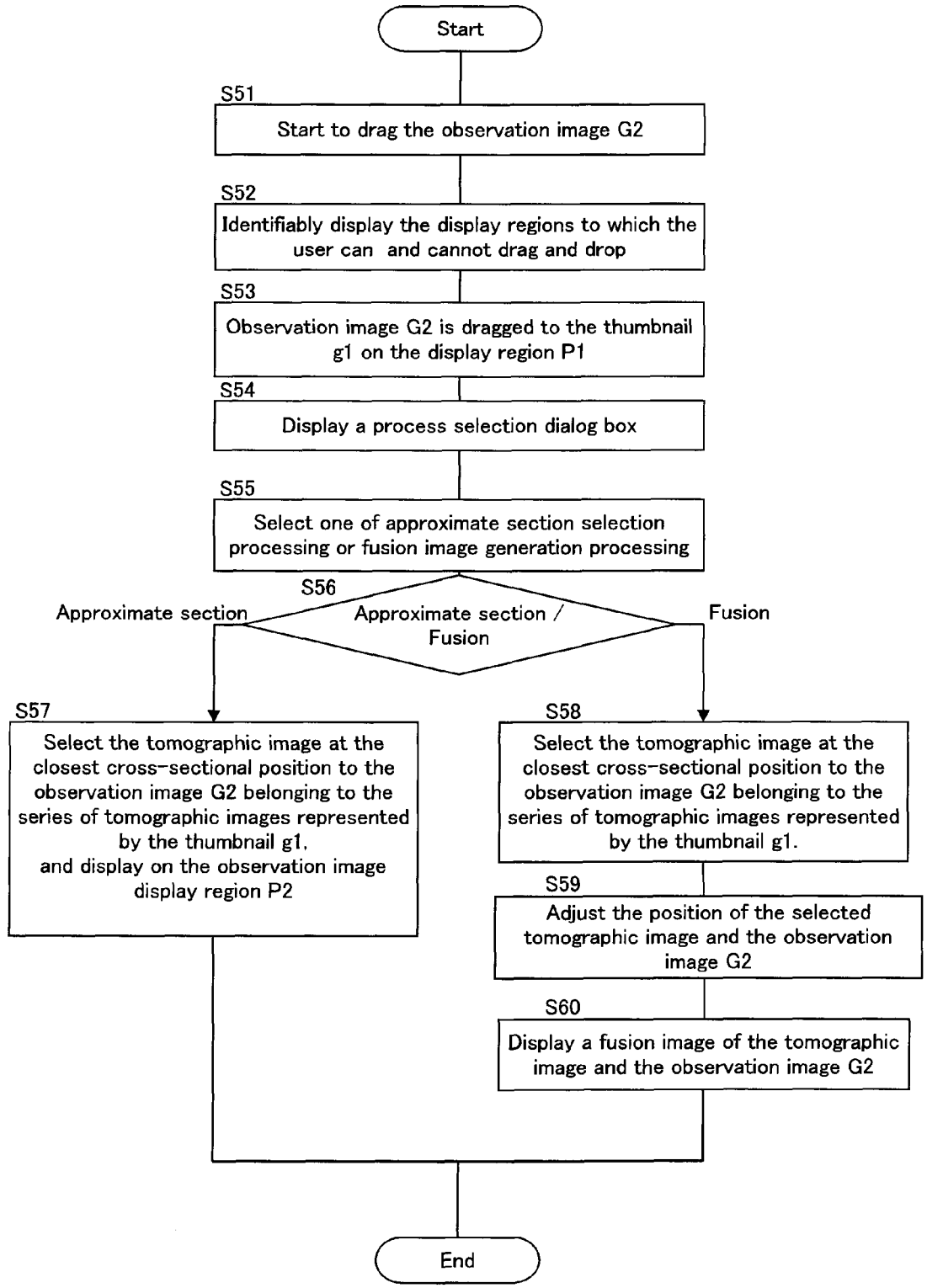
FIG. 14 is a flow chart showing one example of processing performed by one embodiment of the medical image display apparatus according to the present invention.

For example, when the cross-sectional positions of the observation image G3 and G3' are different, the approximate section image selection processing of FIG. 14 will be conducted and a tomographic image of the cross-section that is closest to the observation image G3 from the series to which the observation image G3' belongs will be selected. Then, the observation image of this selected tomographic image is attached by the measurement M' and displayed.

In addition, one example of a case of different cross-sectional directions is herein described in which the observation image G1 of FIG. 15 (axial image) is displayed on the observation image display region P2 and the observation image of FIG. 16 (coronal image) and the measurement M are displayed on the observation image display region P4. In response to the measurement M having been dragged and dropped onto the observation image G1, the tomographic image generation processing of FIG. 12 is performed. Then, based on tomographic images of the series represented by the thumbnail g1 (axial image), a coronal image is generated at the almost identical cross-sectional position to the observation image G3. Then, the observation image of this coronal image is attached by the measurement M' and displayed.

Effect and Advantage

The effects and advantages brought by the medical image display apparatus 1 according to the present embodiment are herein described.

The medical image display apparatus 1 comprises a display component 9, an image data storage component 31, an information storage component 32, and an operation component 10. The display component 9 displays a medical image display screen P in which four image display regions P1 to P4 are predefined. The image storage component 31 stores image data of medical images. The information storage component 32 stores process associating information 32a. The process associating information 32a is information for associating the combination of the image display regions P1 to P4 with the processing contents for the image data of the medical images. Specifically, the operation component 10 may be a mouse.

Furthermore, when two medical images displayed on the different image display regions have been designated by using the operation component 10, that is, when one medical image has been dragged and dropped onto another medical image, the control component 2 of the medical image display apparatus 1 instructs to execute the predetermined processing on one or both of the two medical images. This predetermined processing is processing indicated in the processing content associated by the process associating information 32a with the combination of the image display regions in which the two medical images are displayed.

That is, the medical image display apparatus 1 defines processing content for a combination of image display regions, and performs the processing corresponding to the two image display regions, by dragging and dropping a medical image from a given image display region onto a medical image on another image display region (that is, designate two medical images). The processing content defined for a combination of image display regions may be following processing as shown in FIG. 3.

(1) Display image switch processing: This processing is to be performed when observing a medical image of the study in which a plurality of series is registered. This processing is performed when the thumbnail displayed on the thumbnail display region P1 (or P3) has been dragged and dropped onto the observation image displayed on the observation image display region P2 (or P4). This processing terminates the display of the observation image to which to drag and drop, and displays the observation image in connection with the image data that is based on the thumbnail from which to drag and drop on the observation image display region P2 (or P4).

(2) Parallel display processing: This is performed when observing a medical image of the study in which a plurality of series is registered. This processing is performed when the thumbnail displayed on the thumbnail display region P1 (or P3) has been dragged and dropped onto the observation image displayed on the observation image display region P2 (or P4).

This processing displays the observation image in connection with the image data that is based on the thumbnail from which to drag and drop and the observation image to which to drag and drop on the observation image display region P2 (or P4).

(3) Synchronization between series processing: This is processed when comparing two series of medical images. This processing is performed when the thumbnail displayed on the thumbnail display region P1 (or P3) has been dragged and dropped onto the thumbnail displayed on the thumbnail display region P3 (or P1). This processing associates a medical image included in the series represented by the thumbnail from which to drag and drop (first series) with a medical image included in the series represented by the thumbnail to which to drag and drop (second series) based on incidental information. Specifically, medical images are associated with each other in which the image position information (cross-sectional position information) or the imaging phase information are almost identical. Furthermore, when a medical image of the first series (or the second series) has been displayed on the observation image display region P2 (or P4) via the operation component 10, this processing selects a medical image associated with this medical image from the second series (or the first series) and displays the observation image on the observation image display region P4 (or P2).

(4) Difference image generation processing: This is processed when comparing two series of medical images. This processing is performed when the thumbnail displayed on the thumbnail display region P1 (or P3) has been dragged and dropped onto the thumbnail displayed on the thumbnail display region P3 (P1). This processing associates a medical image included in the series represented by the thumbnail from which to drag and drop (first series), with a medical image included in the series represented by the thumbnail to which to drag and drop (second series) based on incidental information, and generates image data of the difference images between medical images of the first and the second series that have been associated with. Specifically, medical images are associated with each other in which the image position information (cross-sectional position information) or the imaging phase information are almost identical.

(5) Tomographic image generation processing: This is processed when comparing medical images of two studies, particularly in order to obtain a tomographic image of the cross-sectional direction that is not included in one study. This processing is performed when the observation image of the tomographic image displayed on the observation image display region P4 has been dragged and dropped onto the thumbnail displayed on the thumbnail display region P1. This processing generates image data of a new tomographic image of the same cross-sectional direction as the observation image from which to drag and drop based on image data of the tomographic image of the series represented by the thumbnail to which to drag and drop and the incidental information. The obtained tomographic image will be registered as a new series and the thumbnail (representing the series) will be displayed. In addition, this tomographic image will be displayed on the display component 9 automatically or in response to a user request. This tomographic image generation processing is also performed, contrary to the above drag and drop operation, when the thumbnail displayed on the thumbnail display region P1 has been dragged and dropped onto the observation image of the tomographic image displayed on the observation image display region P4. In addition, it is also possible to conduct similar tomographic image generation processing when the observation image of the tomographic image displayed on the observation image display region P2 has been dragged and dropped onto the thumbnail displayed on the thumbnail display region P3. In addition, similar tomographic image generation processing is also possible after the opposite drag and drop operation.

(6). Approximate section image selection processing: This is processed when comparing two series of medical images having the same cross-sectional direction, particularly when comparing two series that have obtained by different modalities or study methods. This processing is performed when the observation image of the tomographic images displayed on the observation image display region P4 has dragged and dropped onto the thumbnail displayed on the thumbnail display region P1. This processing selects a tomographic image at the almost identical cross-sectional position to the observation image from which to drag and drop from the series represented by the thumbnail to which to drag and drop based on the incidental information, and displays the observation image of the selected tomographic image on the observation image display region P2. Incidentally, this processing is also performed, contrary to the above drag and drop operation, when the thumbnail displayed on the thumbnail display region P1 has been dragged and dropped onto the observation image of the tomographic image displayed on the observation image display region P4.

(7) Fusion image generation processing: This is processed when comparing two series of medical images, particularly when comparing two series that have obtained by different modalities or study methods. This processing is performed when the observation image of the tomographic image displayed on the observation image display region P4 has been dragged and dropped onto the thumbnail displayed on the thumbnail display region P1. This processing selects a medical image at the almost identical position to the observation image from which to drag and drop from the series represented by the thumbnail to which to drag and drop based on the image position information in incidental information, and performs position adjustment between the selected medical image and the observation image from which to drag and drop. The medical image and the observation image that have been position-adjusted are displayed on the observation image display region P2 as a fusion image in which one image overlaps another image. Incidentally, this processing is also performed, contrary to the above drag and drop operation, when the thumbnail displayed on the thumbnail display region P1 has been dragged and dropped onto the observation image of the tomographic image displayed on the observation image display region P4.

(8) Annotation attachment processing: This is processed when comparing two series of medical images, particularly when annotation (annotation image) is attached to one medical image. This processing is performed when the annotation displayed attached to the observation image displayed on the observation image display region P4 has been dragged and dropped onto the observation image displayed on the observation image display region P2. This processing attaches an annotation to the observation image to which to drag and drop and displays the same on the observation image display region P2 based on the annotation information of the annotation from which to drag and drop. Incidentally, instead of dragging and dropping an annotation, an observation image with this annotation may be dragged and dropped.

(9) Measurement attachment processing: This is processed when comparing two series of medical images, particularly when measurement result (image) is attached to one medical image. This processing is performed when the measurement displayed attached to the observation image displayed on the observation image display region P4 has been dragged and dropped onto the observation image displayed on the observation image display region P2. This processing attaches measurement to the observation image to which to drag and drop and displays the same on the observation image display region P2 based on the measurement information of the measurement from which to drag and drop. Incidentally, instead of dragging and dropping the measurement, an observation image with this measurement may be dragged and dropped.

These processings have conventionally been conducted by operating the software key arranged on the medical image display screen. Therefore, a disadvantage has occurred in that the software key would be displayed overlapping the medical image and thereby the image would be partially hidden or the display size of the medical image itself would be reduced. According to the medical image display apparatus 1 according to the present embodiment, this processing can be performed only by the drag and drop operation between medical images (i.e. operation for designating medical images). Therefore, according to the medical image display apparatus 1, there is no need to display a software key on the display screen, so it is possible to solve the above disadvantage. In addition, the desired processing can be performed only by a simple operation of designating (dragging and dropping) medical images, and operationality does not become complicated.

In addition, the medical image display apparatus 1, in response to the drag of a medical image on a given image display region having started, identifiably displays the image display region associated with processing content as a combination of the image display regions by the process associating information 32a and the image display region not associated with the same. As a result, a user can easily identify image display regions to which he/she can drag and drop and image display regions to which he/she cannot drag and drop. In this way, according to the medical image display apparatus 1, operationality can be improved in the drag and drop operation for the above various types of operations.

In addition, the medical image display apparatus 1, when a medical image of a given image display region has been dragged to another image display region, displays a dialog box for explaining processing content associated with the combination of these image regions (information of processing content) and thereby operationality can be improved. As a result, the user can easily understand the processing content corresponding to the operation and can operate the desired processing without mistake.

In addition, in the case of having dragged a medical image from a given image display region to another image display region, when the image display regions are associated with two or more processing contents, the medical image display apparatus 1 will display a process selection dialog box for selectably presenting the two or more processing contents (process selection information). As a result, a user can first recognize that the operation is associated with two or more processing contents, and furthermore can easily select a desired one from the two or more processing contents.

The present embodiment described above also comprises various types of configurations that can arbitrarily be applied to the example modifications described below.

Example Modifications

The configuration described above in detail is merely one specific example implementation of the medical image display apparatus according to the present invention. Thus, it is possible to accordingly apply any modification within the scope of the present invention. Hereinafter, example modifications related to the above embodiments are described.

First Example Modification

The first example modification is an example modification of the approximate section image selection processing. The medical image display apparatus related to this example modification has the similar configuration to the above embodiment (cf. FIG. 1). In this regard, however, the tomographic image generating component 6 in this example modification performs the processing for generating image data of a tomographic image having the cross-sectional position between two tomographic images with different cross-sectional positions. This processing is, in other words, an interpolation. The tomographic image generating component 6 is included in one example of the "interpolated tomographic image generating component" of the present invention.

It is assumed that the thumbnail displayed on the thumbnail display region P1 and the observation image displayed on the observation image display region P4 are tomographic images of the same cross-sectional direction. Herein, it is assumed that the thumbnail g1 representing the series of axial images is displayed on the thumbnail display region P1 and the observation image G2 of an axial image is displayed on the observation image display region P4, for example, as shown in FIG. 4.

Incidentally, it is assumed that the series represented by the thumbnail g1 does not include the tomographic image at the same cross-sectional position as the observation image G2 (slice position). In addition, a medical image of the series represented by the thumbnail g1 and the observation image G2 may be each different types of medical images.

A user drags the observation image G2 displayed on the observation image display region P4 and drops the same on the thumbnail g1 by operating the operation component 10. Incidentally, this operation may be the opposite drag and drop operation.

The tomographic image generating component 6 is controlled by the control component 2 to generate image data of a new tomographic image at the almost identical cross-sectional position to the observation image G2 based on image data of a tomographic image of the series represented by the thumbnail g1 and incidental information thereof and the incidental information belonging to the image data of the observation image G2.

More specifically, the tomographic image generating component 6 first specifies the cross-sectional position of the observation image G2 based on the cross-sectional position information in the incidental information of the observation image G2. Next, the tomographic image generating component 6 extracts tomographic images having the cross-sectional position that is close to the cross-sectional position of the observation image G2 with reference to the cross-sectional position information in the incidental information belonging to each tomographic image of the series represented by the thumbnail g1. At this time, for example, two tomographic images having the cross-sectional position located so as to sandwich the cross-sectional position of the observation image G2 are extracted. Then, the tomographic image generating component 6 generates image data of a new tomographic image having the almost identical cross-sectional position to the observation image G2 by performing the known interpolation using image data of the extracted tomographic image.

The control component 2 instructs to display an observation image of this new tomographic image on the observation image display region P2 based on the image data generated by the tomographic image generating component 6.

According to the first example modification, it is also possible to generate an interpolation image at the particular cross-sectional position by a drag and drop operation between medical images. Therefore, the aforementioned disadvantages caused by having the software keys on the display screen will be avoided.

Second Example Modification

The medical image display apparatus related to the second example modification is intended to improve the efficiency in the entire system as well as the effects of the above embodiment by requesting of an external apparatus (viewer or the like) to execute the predetermined processing.

Figure 21:
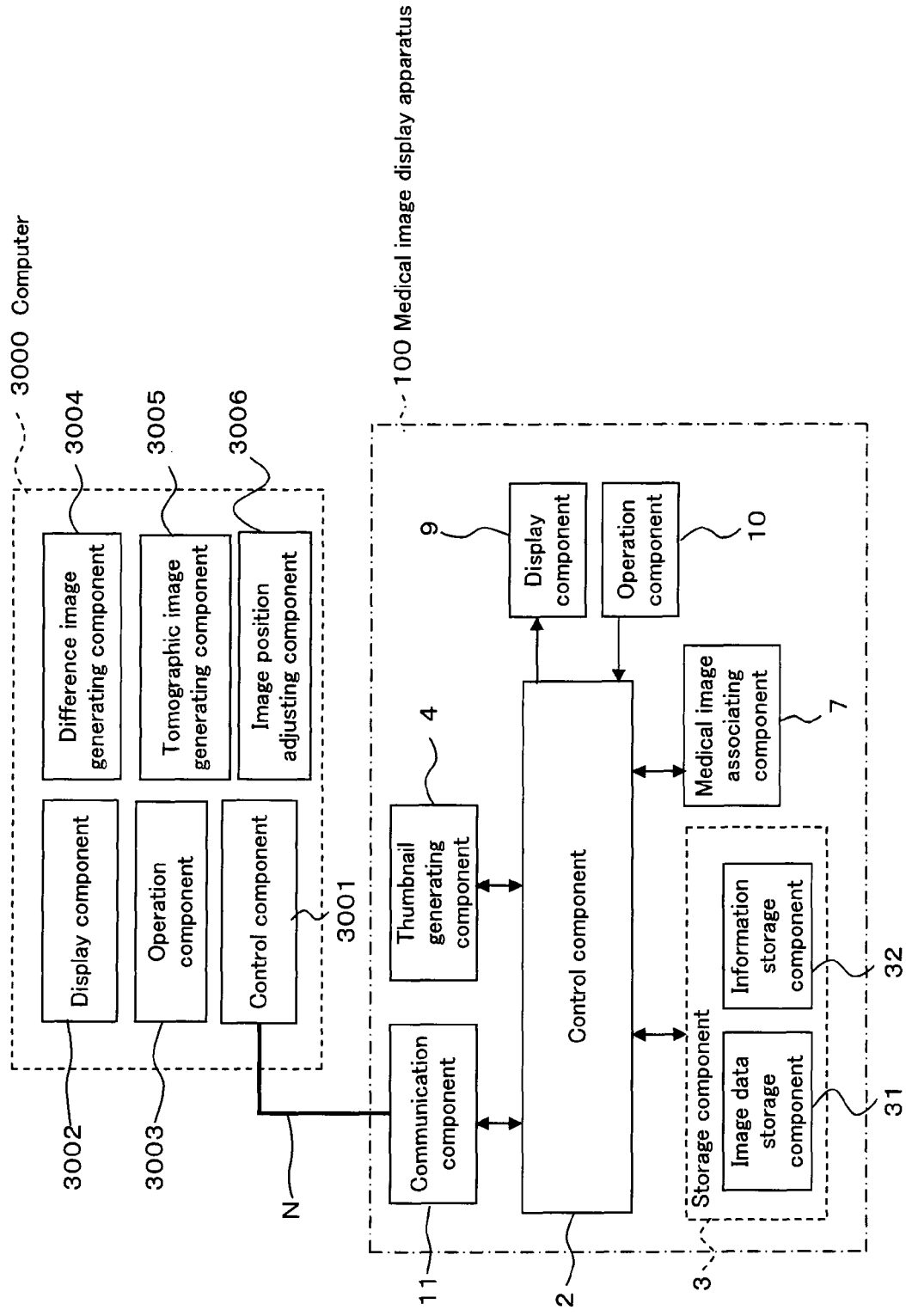
FIG. 21 is a block diagram showing one example of the entire configuration of a modification example of one embodiment of the medical image display apparatus according to the present invention.

FIG. 21 shows one example of the medical image display apparatus related to this example modification. The medical image display apparatus 100 shown in FIG. 21 is provided with a control component 2, a storage component 3, a thumbnail generating component 4, a medical image associating component 7, a display component 9, an operation component 10, and a communication component 11 as is in the case with the medical image display apparatus 1 in the above embodiment. The communication component 11 is included in one example of the "communication component" of the present invention. Incidentally, there is no need to be provided with a difference image generating component 5, a tomographic image generating component 6, and an image position adjusting component 8.

The medical image display apparatus 100 is connected to a computer 3000 via a network N. The computer 3000 is, for example, a server on the network N, a viewer for interpretation, and so on. The computer 3000 is preferably a computer with higher processing capacity than the medical image display apparatus 100. In that case, a plurality of apparatuses similar to the medical image display apparatus 100 may be connected to the computer 3000. Incidentally, illustration of the medical image diagnosis apparatus 1000A and 1000B and the medical image database 2000 that have been connected to the network N is omitted in FIG. 21.

The computer 3000 comprises a control component 3001, a display component 3002, and an operation component 3003 as is the case with a usual computer. The storage unit of the computer 3000 such as a hard disk drive stores a computer program for generating image data of a difference image, a computer program for generating image data of a tomographic image by MPR or the like, and a computer program for performing position adjustment of images. In addition, the control component 3001 comprises communication units such as a LAN card and a MODEM.

A microprocessor of the computer 3000 executes the computer programs so as to implement a difference image generating component 3004, a tomographic image generating component 3005, and an image position adjusting component 3006. The difference image generating component 3004, the tomographic image generating component 3005, and the image position adjusting component 3006 each act similar to the difference image generating component 5, the tomographic image generating component 6, and the image position adjusting component 8, respectively, in the above embodiment. Incidentally, the computer 3000 does not necessarily consist of a single computer, but may be distribute these functions to two or more computers.

This example modification provides an example of each method of difference image generation processing, tomographic image generation processing, and fusion image generation processing in the above embodiment.

Example Modification of the Difference Image Generation Processing

First, an example modification of the difference image generation processing is described with reference to FIG. 4. For this processing, a user drags the thumbnail g1 displayed on the thumbnail display region P1 and drops the same onto the thumbnail g2 displayed on the thumbnail display region P3 by operating the operation component 10 (mouse). Incidentally, it may be designed to conduct the opposite drag and drop operation.

After this drag and drop operation, the medical image associating component 7 associates a medical image included in the series represented by the thumbnail g1 (first series) with a medical image included in the series represented by the thumbnail g2 (second series) in a manner similar to the above embodiment.

The control component 2 sends signal for requesting the generation of image data of the difference image between the associated medical images (request information) to the communication component 11. To the communication component 11, image data of the medical image included in the first series medical images and image data of the medical image included in the second series medical images are also sent therewith. The communication component 11 sends the above data to the computer 3000 via the network N.

The control component 3001 of the computer 3000 receives data from the medical image display apparatus 100 and sends the same to the difference image generating component 3004. The difference image generating component 3004 generates image data of a difference image between the associated medical images based on this data. The generated image data is sent to the medical image display apparatus 100 by the control component 3001.

The medical image display apparatus 100 receives the image data that has been sent from the computer 3000. The control component 2 instructs to display a difference image based on this image data on the observation image display region P2. This difference image can also be displayed on the display component 3002 of the computer 3000 if necessary.

Example Modification of Tomographic Image Generation Processing

Next, an example modification of the tomographic image generation processing is described with reference to FIG. 10. For this processing, a user drags the observation image G3 of the tomographic image displayed on the observation display region P4 and drops the same onto the thumbnail g1 displayed on the thumbnail display region P1 by operating the operation component 10 (mouse). Incidentally, it may be designed to conduct the opposite drag and drop operation.

After this drag and drop operation, the control component 2 sends signal for requesting the generation of image data of the tomographic image of the same cross-sectional image as the observation image G3 (request information) to the communication component 11. To the communication component 11, image data of the tomographic image of the series represented by the thumbnail g1 and incidental information thereof and incidental information of the observation image G3 are also sent therewith. The communication component 11 sends the above data to the computer 3000 via the network N.

The control component 3001 of the computer 3000 receives data from the medical image display apparatus 100 and sends the same to the tomographic image generating component 3005. The tomographic image generating component 3005 generates image data of the intended tomographic image based on this data. The generated image data is sent to the medical image display apparatus 100 by the control component 3001.

The medical image display apparatus 100 receives the image data sent from the computer 3000. The control component 2 instructs to display a tomographic image based on this image data on the observation image display region P2. This tomographic image can be displayed also on the display component 3002 of the computer 3000, if necessary.

Example Modification of the Fusion Image Generation Processing

Next, an example modification of the fusion image generation processing is described with reference to FIG. 10. For this processing, a user drags the observation image G2 of the tomographic image displayed on the observation image display region P4 and drops the same onto the thumbnail g1 displayed on the thumbnail display region P1 by operating the operation component 10 (mouse). Incidentally, it may be designed to conduct the opposite drag and drop operation.

After this drag and drop operation, the control component 2, based on the cross-sectional position information in the image position information of a tomographic image in the series represented by the thumbnail g1 and the cross-sectional position information in the image position information of the observation image G2, selects a tomographic image at the almost identical cross-sectional position to the observation image G2 from the above series.

Next, the control component 2 sends image data and image position information of the selected tomographic image, image data and image position information of the observation image G2, and signal for requesting the position adjustment between the two images (request information) to the communication component 11. The communication component 11 sends these data to the computer 3000 via the network N.

The control component 3001 of the computer 3000 receives data from the medical image display apparatus 100 and sends the same to the image position adjusting component 3006. The image position adjusting component 3006 adjusts the position between the tomographic image selected from the series represented by the thumbnail g1 and the observation image G2 based on the image position information. The position-adjusted image data is sent to the medical image display apparatus 100 by the control component 3001.

Incidentally, this image data may be a single image data obtained by applying the transparency value adjustment or the like as well as the position adjustment and synthesizing two or more image data. In addition, this image data may be data comprising image data of the selected tomographic image, image data of the observation image G2, and the data indicating the position adjustment results between the two image data (such as the travel distance of coordinate values).

The medical image display apparatus 100 receives image data that has been sent from the computer 3000. The control component 2 instructs to display a fusion image based on this image data on the observation image display region P2. This fusion image may be displayed also on the display component of the computer 3000, if necessary.

Third Example Modification

While the processing described in the above embodiments are performed after having designated two medical images, it is also possible to designate three or more medical images and to perform the predetermined processing. In the third to sixth example modifications, one example of the configuration in which three or more medical images are designated is described. Incidentally, a specific example of designating feature of three or more medical images is described in the sixth example modification.

This example modification is an example modification of the difference image generation processing in the above embodiment. In the interpretation work of medical images, images of a plurality of studies that have been implemented may be observed at one time. Particularly, images at an identical site (e.g., identical cross-positional position) may be observed at one time. In such a case, these images are displayed on the medical image display screen side by side.

Although the illustration is omitted, it is assumed that tomographic images at the same cross-sectional position having been obtained at h time (h≥3) studies and implemented thus far are displayed in this example modification. Incidentally, as a display feature of these tomographic images, for example, the tomographic image G1 of the latest study is displayed on the observation image display region P2 (of the left) of the medical image display screen P in the above embodiment, and the tomographic images G2 to Gh of earlier studies are displayed on the observation image display region P4 (of the right) thereof. In addition, it is also possible to establish a display region for each study, and on each display a tomographic image obtained in each study.

A user designates the h tomographic images G1 to Gh by operating the operation component 10. The difference image generating component 5 generates image data of difference images for each combination of the designated tomographic images G1 to Gh. That is, the difference image generating component 5 generates image data of the difference image S (i, j) for each pair (Gi, Gj) (i, j=1 to h, i≠j) of h tomographic images.

The thumbnail generating component 4 generates image data of the thumbnail s (i, j) of each difference image S (i, j) based on the image data of the generated difference image S (i, j). The control component 2 generates a list of difference images as shown in FIG. 22 based on this image data. A thumbnail s(i, j) corresponding to each pair of tomographic images (Gi, Gj) is arranged in a matrix state in this list of difference images. The user can display the difference image S (i, j) corresponding to a desired thumbnail s(i, j) by designating (such as by clicking) the thumbnail s(i, j).

Fourth Example Modification

In the fourth example modification, the display image switch processing in the case of designating three or more medical images is described. Incidentally, while the configuration for switching displaying images of three studies is described in this example modification, similar processing is also possible for four or more studies.

It is assumed that a tomographic image of present study, a tomographic image of the last study, and a tomographic image of the study before last are displayed on the display component 9. In addition, it is assumed that each study includes a series of tomographic images in the almost same cross-sectional direction and position.

A user observes the tomographic image of present study, for example. At this time, the user operates to selectably display the images in order to observe the tomographic images included in the series of present study. Assume that, for example, a suspicious shadow was found during observation of a given tomographic image (referred to as noted image). The user can designate tomographic images from the present study, the last study, and the study before last (or display regions thereof) by operating the operation component 10.

The control component 2 selects a tomographic image at the almost identical cross-sectional position to the noted image from the series from the last study and the study before last. For this processing, incidental information may be referred to in the similar way to the above embodiment.

Furthermore, the control component 2 terminates the display of tomographic images from the last study and the study before last that have already been displayed, and instructs to display the selected tomographic images from the last study and the study before last. As a result, tomographic images from the last study and the study before last at the almost identical cross-sectional position to the noted image are displayed on the display component 9 along with the noted image. At this time, it is also possible to generate an appropriate tomographic image based on tomographic images of that series and to display the same instead of selecting a tomographic image at the almost identical cross-sectional position from the series. Incidentally, the generation processing of the tomographic image is performed by the tomographic image generating component 6.

Fifth Example Modification

In the fifth example modification, the tomographic image generation processing in the case of designating three or more medical images is described. It is assumed that tomographic images in the three studies are displayed, as is the case with the fourth embodiment.

A user displays and observes, for example, a MPR image (or an oblique image) of the current tomographic image. This MPR image is generated by the tomographic image generating component 6 based on the series of current tomographic images. In addition, to this MPR image, the incidental information representing the cross-sectional information indicating its cross-sectional position or the like is provided.

The user designates the current MPR image, and tomographic images of the last study and the study before last by operating the operation component 10. The tomographic image generating component 6 generates a MPR image at the almost identical cross-sectional position from the last study based on the cross-sectional position of the designated current MPR image and the series of the last study. A MPR image at the almost identical cross-sectional position from the study before last is also generated in a similar way.

The control component 2 instructs the display component 9 to display the newly generated MPR images from the last study and the study before last in place of the tomographic images from the last study and the study before last that have already been displayed. As a result, MPR images from the present study, the last study, and the study before last at the almost identical cross-sectional position will be displayed.

Sixth Example Modification

In the sixth example modification, a specific example of designating feature of three or more medical images is described.

The first feature is to drag one medical image (or a display region; hereinafter same as above) and drop the same on two or more other medical images. At this time, for example, for each series to which that two or more medical images belong, the same processing as the series to which that one medical image belongs will be performed. In addition, it is performed the processing for generating a new medical image (such as a difference image and a fusion image) based on each series to which that two or more medical images belong and the series to which that one medical image belongs. The operational feature below also performs similar processing.

The second feature is to drag two or more medical images in a lump and drop the same on one medical image. At this time, it is possible, for example, to operate the control key on the keyboard and the mouse at the same time in order to drag two or more medical images in a lump.

The third feature is to employ a dialog box for presenting a practicable processing. In response to the operation described in the first or the second feature, the similar dialog box to the above embodiment is displayed. A user selects a desired processing for execution.

In addition, it is also possible to designate three or more medical images as follows. First, a dialog box is instructed to display after having dragged and dropped one medical image on another medical image, as is the case with the above embodiment. The dialog box will be continuously displayed until the predetermined operation by a user. This dialog box is provided with a region for adding medical images (addition region) and an addition terminating key. The user drags and drops yet another medical image in the addition region. In this way, all the desired medical images are dropped onto the addition region and then the addition terminating key is clicked. As a result, two or more medical images from which and to which to drag and drop will be designated, and the processing presented in the dialog box will be performed.

Incidentally, it is also possible to selectably present a plurality of processing in the dialog box (e.g. tags described above) to perform the selected processing. In addition, it is also possible, instead of providing the addition terminating key, to continuously display the dialog box while operating the predetermined key on the keyboard during which time the desired medical images can be added. On the contrary, it is also possible to continuously display the dialog box until the predetermined operation is instructed during which time medical images can be added.

According to the third to sixth example modifications, it is possible to the solve disadvantages due to the software key and at the same time avoid complicating the operating procedure as is the case with the above embodiment.

Seventh Example Modification

Figure 23:
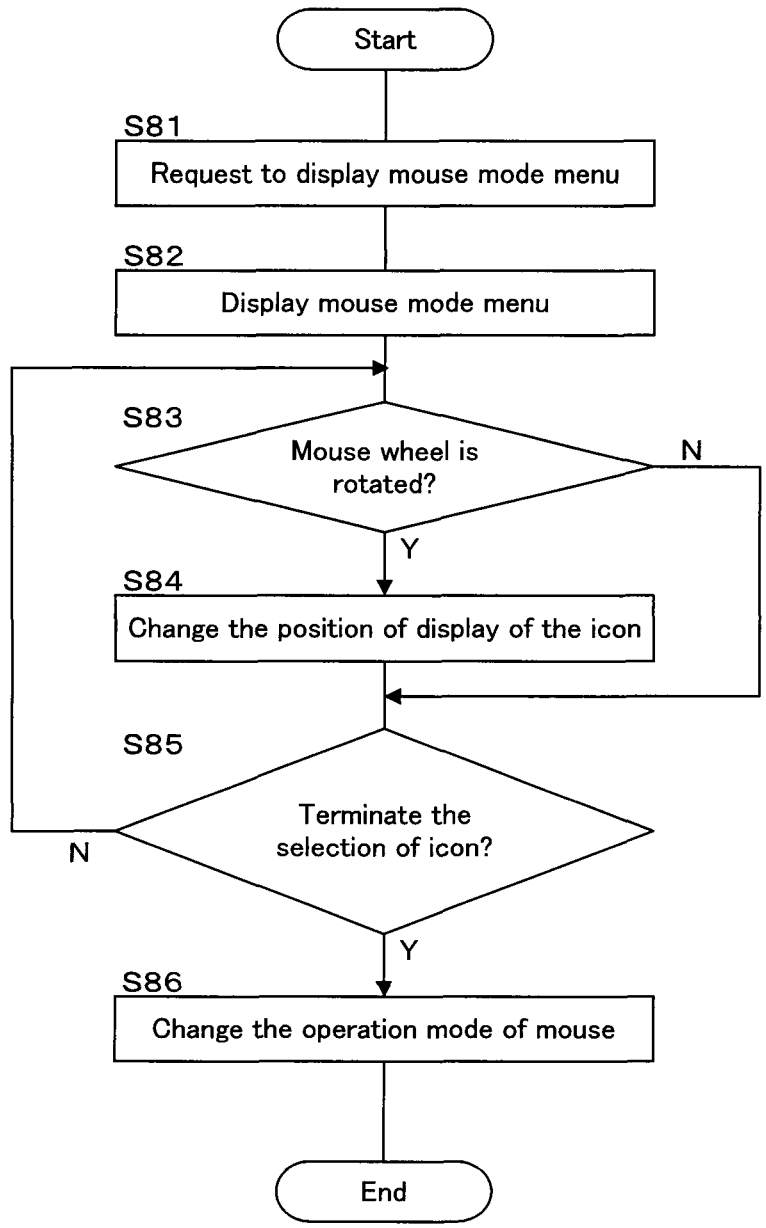
FIG. 23 is a flow chart showing one example of processing performed by a modification example of one embodiment of the medical image display apparatus according to the present invention.

In the seventh example modification, the operationality of the mouse as the operation component 10 is improved. The mouse is employed for various operations such as an operation for changing the gray scale of a display image, an operation for enlarging, reducing, rotating and panning a display image, and an operation for entering an annotation into a display image. Hereinafter, one example of the configuration for employing one mouse for various operations is described with reference to FIG. 23 to FIG. 25.

Figure 24:
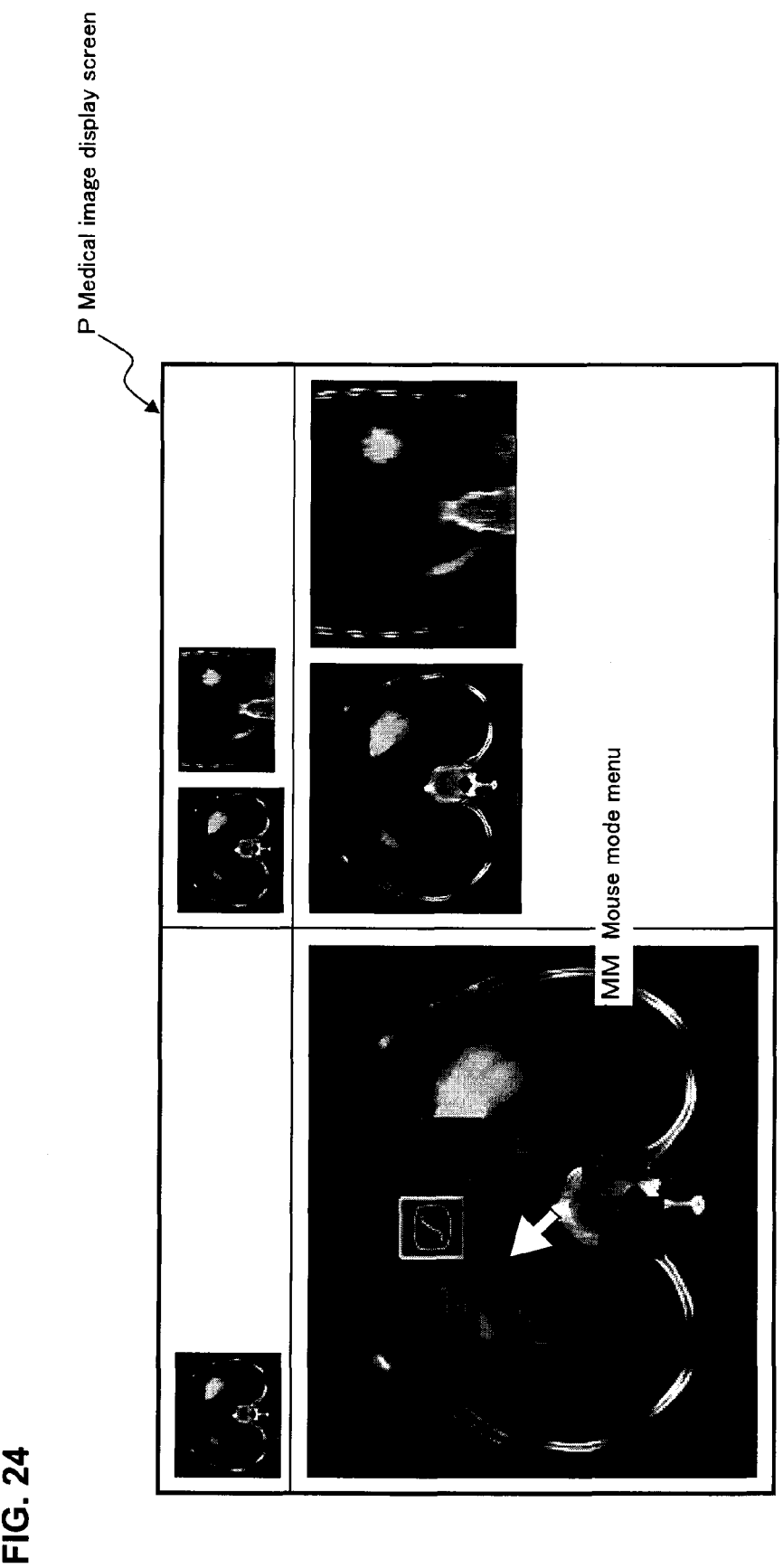
FIG. 24 is a diagram showing one example of display feature of the medical image display screen according to a modification example of one embodiment of the medical image display apparatus according to the present invention.

For example, when the medical image display screen P is in the display state shown in FIG. 10, in response to the predetermined operation via the operation component 10 by the user (S81), the control component 2 instructs the display component 9 to display a mouse mode menu MM as shown in FIG. 24 (S82).

As operations of the step S81, for example, it is possible to apply an operation for rotating a mouse wheel while pressing a control key on the keyboard or an operation for double clicking on the screen of the medical image display screen P with the mouse. Herein, the former operation will be employed.

The mouse mode menu MM shown at step S82 includes a plurality of (herein 8) icons indicating operations by the mouse. These icons are arranged in a almost circular pattern. Among these icons, an icon at the 12 o'clock position is the selected icon.

Eight icons presented on the mouse mode menu MM are in turn clockwise described from the icon at the 12 o'clock position in FIG. 24: (1) an icon corresponding to the changing operation of the window level and the window width of the displayed medical image, (2) an icon corresponding to the operation for entering an oval annotation, (3) an icon corresponding to the operation for entering a rectangular annotation, (4) an icon corresponding to the operation for entering an arrow-shaped annotation, (5) an icon corresponding to the operation for designating a plurality of objects on the display screen (such as medical images), (6) an icon corresponding to the drag operation, (7) an icon corresponding to the operation for enlarging/reducing images, and (8) an icon corresponding to the operation for panning images.

Figure 25:
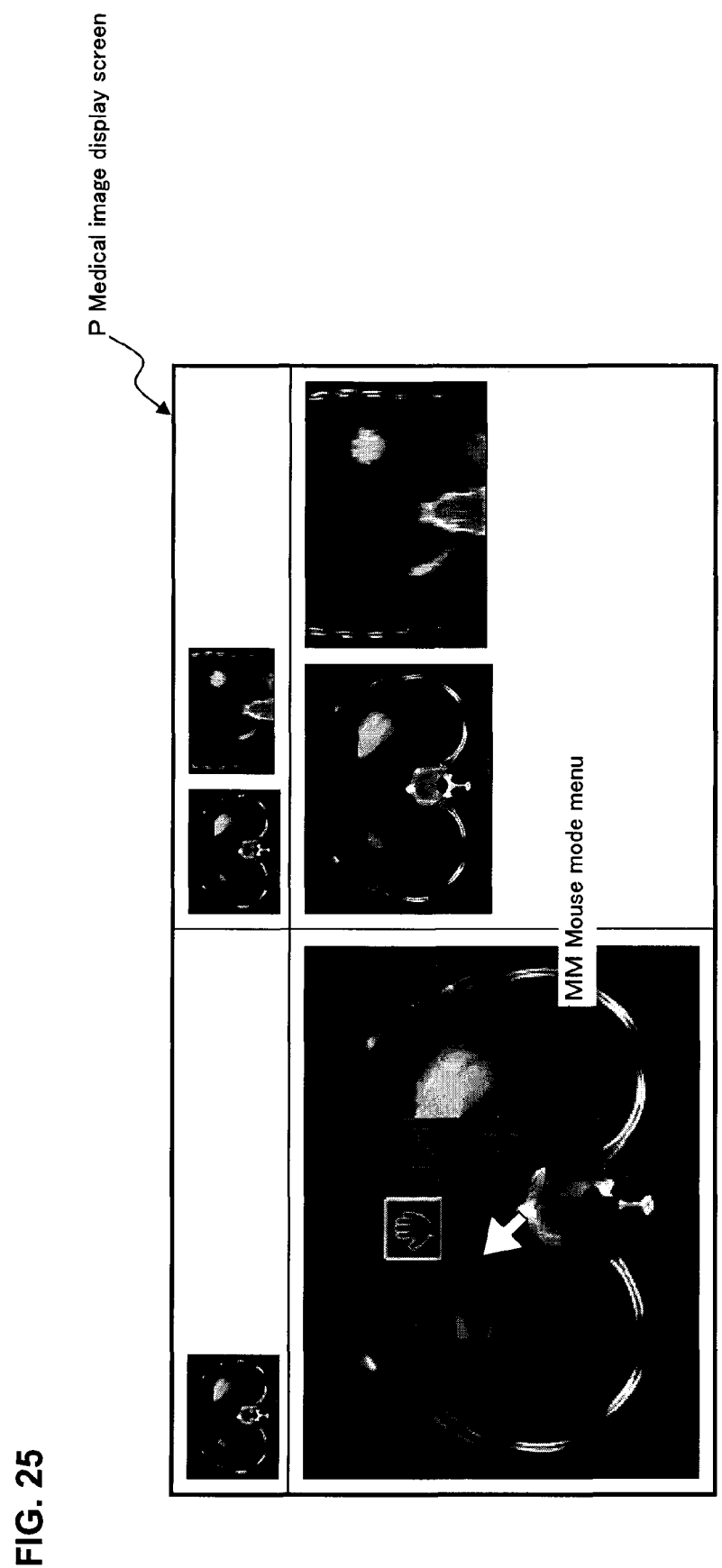
FIG. 25 is a diagram showing one example of display feature of the medical image display screen according to a modification example of one embodiment of the medical image display apparatus according to the present invention.

When the user rotates the mouse wheel (S83; Y), the control component 2 instructs to display the eight icons, for example, rotating clockwise depending on their rotation angle (S84). The user rotates the mouse wheel so as to arrange the icon corresponding to the desired mouse operation at the 12 o'clock position. FIG. 25 shows the display state of clockwise rotation by three icons from the arrangement state of icons shown in FIG. 24. In the display state of FIG. 25, an icon corresponding to the drag operation is selected.

After the icon of the desired mouse operation is selected, the user operates to unlock the pressed state of the control key or the like so as to request the termination of the icon selection work (S85; Y).

The control component 2 changes the setting of the operation mode of the mouse for an operation corresponding to the selected icon with the mouse (S86).

While the icons are arranged corresponding to each operation mode in a circular pattern and the mode selection in the changing processing of the operation mode of the mouse described above is selected, the structure of arrangement is arbitrary. In addition, it is also possible, instead of using icons, to display a mouse mode selection dialog box such as the process selection dialog box D1 shown in FIG. 7 to select the desired process from tabs corresponding to each operation mode. In addition, it is possible to employ any method for selectably presenting the desired selection from a plurality of choices of operation content such as a pull-down menu and a software key. Information for selectably presenting a plurality of operation modes of the mouse as above is included in the "operation content selection information" of the present invention.

In addition, the operation method for selecting a desired operation mode is not limited to the above configuration, but it is also possible to apply any operational structure using the operation component 10.

Other Modifications

Although the medical images is designated by dragging and dropping a medical image onto another medical image in the above embodiment, the designation method of medical images is not limited to this. For example, the designation is possible such as by clicking each medical image. In addition, the order to designate two medical images can also be accordingly set.

The above embodiment is designed for the processing associated with the image display region in which two medical images are displayed by designating those images, but not limited to this. For example, the processing is also possible by designating the medical image to be processed and the image display region in which another medical image is displayed. That is, the design may be such that, when a user designates a medical image displayed on the first image display region among a plurality of image display regions and the second image display region by operating the operation component 10, the control component 2 instructs to execute on image data of this medical image the processing indicated in the processing content associated by the process associating information 32a with the combination of the first image display region and the second image display region.

For example, the display image switch processing may be modified as follows: when the thumbnail displayed on the thumbnail display region P1 (or P3) and the observation image display region P2 (or P4) are designated, the display of the observation image displayed on the observation image display region P2 (or P4) is terminated and an observation image of a medical image of the series represented by the designated thumbnail is displayed on the observation image display region P2 (or P4).

In addition, the parallel display processing may be modified as follows: when the thumbnail displayed on the thumbnail display region P1 (or P3) and the observation image display region P2 (P4) are designated, an observation image of a medical image of the series represented by the designated thumbnail is displayed on this observation image display region P2 (or P4) along with the observation image already displayed on the observation image display region P2 (or P4).

In addition, while "reduced image" of the present invention in the above embodiment is supported by the thumbnail, the "reduced image" may also be an image obtained simply by reducing the observation image.

What is claimed is:

1. A medical image display apparatus comprising:
a display component having a medical image display screen having a plurality of image display regions including a plurality of reduced image display regions and a plurality of observation display regions, each reduced image display region configured to show a reduced image of a medical image obtained by scanning of a medical image diagnosis apparatus, each observation display region configured to show in correspondence with each reduced image display region a medical image included in a same series as the medical image shown as the reduced image;
an associating information storage component configured to store in association with each other respective combinations from reduced image display regions and observation display regions with respective image processing to be performed in relation to said respective combinations;
a selecting component configured to select two regions from the reduced image display regions and the observation display regions, refer the selected two regions to the associating information storage component, and access the image processing stored in the associating information storage component in association with the combination of the selected two regions; and
an image processor configured to perform the image processing accessed by the selecting component on the medical image displayed as the selected two regions, wherein
the associating information storage component is configured to associate each of a combination of a reduced image display region and an observation display region, a combination of reduced image display regions, and a combination of observation display regions with the image processing to be performed.

2. A medical image display apparatus according to claim 1, wherein an image data storage component further stores incidental information of the medical images, and an image processor instructs to execute said processing based on the incidental information of each of said designated at least two medical images.

3. A medical image display apparatus according to claim 2, further comprising:

a reduced image generating component operable to generate image data of a reduced image of the medical image based on the image data of said medical image stored in said image data storage component, wherein said plurality of image display regions includes a first reduced image display region in which a first reduced image generated for a representative image of a series of medical images is displayed, a second reduced image display region in which a second reduced image generated for a representative image of other series of medical images is displayed, a first observation image display region in which an observation image of said series of medical images provided for observation by a user is displayed, and a second observation image display region in which an observation image of said other series of medical images is displayed, wherein said image processor comprises a medical image associating component, in response to designation of said first reduced image and said second reduced image, operable to associate said medical image included in said series of medical images with said medical image included in said other series of medical images, based on said stored incidental information, and wherein said image processor, when one medical image of said series of medical images is displayed on said first observation image display region, selects a medical image associated with said one medical image from said other series of medical images and instructs to display the observation image of said selected medical image on said second observation image display region.

4. A medical image display apparatus according to claim 3, wherein said incidental information includes image position information indicating the position of a medical image, and said medical image associating component associates the medical images when the positions indicated in the image position information of the medical images are substantially identical.

5. A medical image display apparatus according to claim 4, wherein said series of medical images are a series of tomographic images of an object, said other series of medical images are other series of tomographic images of the object, said image position information includes a cross-sectional position information indicating the cross-sectional position of a tomographic image, and said medical image associating component associates the medical images when the cross-sectional positions indicated in the cross-sectional position information of the tomographic images are substantially identical.

6. A medical image display apparatus according to claim 3, wherein said incidental information includes imaging phase information indicating an imaging phase of medical images, and said medical image associating component associates the medical images when the imaging phases indicated in the imaging phase information of the medical images are substantially identical thereto.

7. A medical image display apparatus according to claim 2, further comprising:

a reduced image generating component operable to generate image data of a reduced image of the medical image based on the image data of said medical image stored in said image data storage component, and a difference image generating component operable to generate image data of a difference image of two different medical images based on the image data of said two medical images, wherein said plurality of image display regions includes a first reduced image display region in which a first reduced image generated for a representative image of a series of medical images is displayed and a second reduced image display region in which a second reduced image generated for a representative image of the other series of medical images is displayed, wherein said image processor comprises a medical image associating component, in response to designation of said first reduced image and said second reduced image, operable to associate said medical image included in said series of medical images with said medical image included in said other series of medical images, based on said stored incidental information as said process, and wherein said image processor generates image data of a difference image of said medical image included in said associated series of medical images and said medical image included in said other series of medical images by controlling said difference image generating component.

8. A medical image display apparatus according to claim 7, wherein said incidental information includes image position information indicating the position of a medical image, and said medical image associating component associates the medical images when the positions indicated in the image position information of the medical images are substantially identical.

9. A medical image display apparatus according to claim 7, wherein said incidental information includes imaging phase information indicating an imaging phase of medical images, and said medical image associating component associates the medical images when the imaging phases indicated in the imaging phase information of the medical images are substantially identical thereto.

10. A medical image display apparatus according to claim 2, wherein said medical image display apparatus is connected to a computer having a difference image generating component operable to generate image data of a difference image of two different medical images based on the image data of said two medical images via a network, further comprising:

a reduced image generating component operable to generate image data of a reduced image of the medical image based on the image data of said medical image stored in said image data storage component, and a communication component for communicating with said computer via said network, wherein said plurality of image display regions includes a first reduced image display region in which a first reduced image generated for a representative image of a series of medical images is displayed and a second reduced image display region in which a second reduced image generated for a representative image of other series of medical images is displayed, and wherein said image processor includes a medical image associating component, when said first reduced image and said second reduced image are designated, operable to associate said medical image included in the series of medical images with said medical image included in other series of medical images, based on said stored incidental information as said process, and wherein said image processor instructs said difference image generating component to generate image data of the difference image by sending said image data of the medical image included in said series of medical images, said image data of the medical image included in said other series of medical images, and request information for requiring the generation of image data of said difference image of the associated medical images to said computer via said network.

11. A medical image display apparatus according to claim 10, wherein said incidental information includes image position information indicating the position of a medical image, and said medical image associating component associates the medical images when the positions indicated in the image position information of the medical images are substantially identical.

12. A medical image display apparatus according to claim 10, wherein said incidental information includes imaging phase information indicating an imaging phase of medical images, and said medical image associating component associates the medical images when the imaging phases indicated in the imaging phase information of the medical images are substantially identical thereto.

13. A medical image display apparatus according to claim 2, wherein the image data of the medical images stored in said image data storage component includes image data of tomographic images of an object, wherein the medical image display apparatus further comprises:

a reduced image generating component operable to generate image data of a reduced image of the tomographic image based on the image data of said stored tomographic image, and a tomographic image generating component operable to generate image data of a tomographic image of the different cross-sectional direction from said stored tomographic image based on the image data of said tomographic image, wherein said plurality of image display regions includes a reduced image display region in which a reduced image generated for a representative image of a series of tomographic images is displayed and an observation image display region in which an observation image of a tomographic image of different cross-sectional direction from said series of tomographic images is displayed, that is provided for observation by a user, said image processor, when the reduced image displayed on said reduced image display region and the observation image of the tomographic image displayed on said observation image display region are designated, instructs said tomographic image generating component as said process to generate image data of a new tomographic image of the same cross-sectional direction as said designated observation image based on the image data of the tomographic image included in said series of tomographic images and said stored incidental information.

14. A medical image display apparatus according to claim 13, wherein said plurality of image display regions further includes other observation display regions in which an observation image of said series of tomographic images is displayed, and said image processor instructs to display an observation image of said new tomographic image based on the image data generated by said tomographic image generating component on said other observation image display regions.

15. A medical image display apparatus according to claim 13, wherein said reduced image generating component generates image data of a reduced image of said new tomographic image based on the image data generated by said tomographic image generating component, and said image processor instructs said image data storage component to store the image data of said new tomographic image and instructs to display the reduced image of said generated said new tomographic image on said reduced image display region.

16. A medical image display apparatus according to claim 2, wherein said medical image display apparatus is connected via a network to a computer having a tomographic image generating component operable to generate image data of a tomographic image of the different cross-sectional direction from the tomographic image of an object based on the image data of said tomographic image, wherein the image data of the medical images stored in said image data storage component includes image data of tomographic images of an object, wherein said medical image display apparatus further comprises a reduced image generating component operable to generate image data of a reduced image of the tomographic image based on the image data of said stored tomographic image, and a communication component for communicating with said computer via said network, wherein said plurality of image display regions includes a reduced image display region in which a reduced image generated for a representative image of a series of tomographic images is displayed and an observation image display region in which an observation image of a tomographic image of different cross-sectional direction from said series of tomographic images is displayed, that is provided for observation by a user, said image processor, when the reduced image displayed on said reduced image display region and the observation image of the tomographic image displayed on said observation image display region are designated, instructs said communication component as said process to send to said computer via said network the image data of the tomographic image included in said series of tomographic images, said stored incidental information, and request information for requesting the generation of image data of said new tomographic image of the same cross-sectional direction as said designated observation image based on said image data and said incidental information, so that said tomographic image generating component generates image data of new tomographic images.

17. A medical image display apparatus according to claim 16, wherein
said plurality of image display regions further includes other observation display regions in which an observation image of said series of tomographic images is displayed, and
said image processor instructs to display an observation image of said new tomographic image based on the image data generated by said tomographic image generating component on said other observation image display regions.

18. A medical image display apparatus according to claim 16, wherein
said reduced image generating component generates image data of a reduced image of said new tomographic image based on the image data generated by said tomographic image generating component, and
said image processor instructs said image data storage component to store the image data of said new tomographic image and instructs to display the reduced image of said generated said new tomographic image on said reduced image display region.

19. A medical image display apparatus according to claim 2, further comprising:
a reduced image generating component operable to generate image data of a reduced image of the medical image based on the image data of said medical image stored in said image data storage component,
wherein said medical image includes a tomographic image of an object,
said plurality of image display regions includes a reduced image display region in which a reduced image generated for a representative image of a series of tomographic images is displayed, a first observation image display region in which an observation image of said series of tomographic images provided for observation by a user is displayed, and a second observation image display region in which an observation image of a tomographic image of the same cross-sectional direction as said series of tomographic images is displayed, and
said image processor, when a reduced image displayed on said reduced image display region and an observation image of the tomographic image displayed on said second observation image display region are designated, as said process, selects a tomographic image at the substantially identical cross-sectional position to said designated observation image from said series of tomographic images based on said stored incidental information and instructs to display the observation image of said selected tomographic image on said first observation image display region.

20. A medical image display apparatus according to claim 19, wherein
the image data of said series of tomographic images and the image data of said tomographic images of the same cross-sectional tomographic images are different types of medical images.

21. A medical image display apparatus according to said claim 2, wherein
said medical image includes a tomographic image of an object,
wherein said medical image display apparatus further comprises a reduced image generating component operable to generate image data of a reduced image of the medical image based on the image data of said medical image stored in said image data storage component, and
an interpolated tomographic image generating component operable to generate image data of a tomographic image having the cross-sectional position between two tomographic images having different cross-sectional positions,
wherein said plurality of image display regions includes a reduced image display region in which a reduced image generated for a representative image of a series of tomographic images is displayed, a first observation image display region in which an observation image of said series of tomographic images provided for observation by a user is displayed, and a second observation image display region in which an observation image of the tomographic image of the same cross-sectional direction as said series of tomographic images is displayed, and
said image processor, when the reduced image displayed on said reduced image display region and the observation image of the tomographic image displayed on said second observation image display region is designated, instructs said interpolated tomographic image generating component as said process, to generate image data of a new tomographic image at the substantially identical cross-sectional position to said designated observation image based on the image data of the tomographic image included in said series of tomographic images and said stored incidental information, and instructs to display the observation image of said new tomographic image on said first observation image display region.

22. A medical image display apparatus according to claim 21, wherein
the image data of said series of tomographic images and the image data of said tomographic images of the same cross-sectional tomographic images are different types of medical images.

23. A medical image display apparatus according to claim 2, wherein
said incidental information includes image position information indicating the position of a medical image, and
said image data storage component stores two or more different types of medical images,
wherein said medical image display apparatus further comprises
a reduced image generating component operable to generate image data of a reduced image of the medical image based on the image data of said medical image stored in said image data storage component, and
an image position adjusting component operable to adjust the positions of different types of medical images, based on each image data of said different types of medical images and said image position information, wherein
said plurality of image display regions includes a reduced image display region in which a reduced image generated for a representative image of a series of medical images is displayed, and an observation image display region in which an observation image of the medical image having the same cross-sectional direction as said series of medical images and being the different types of medical image from said series of medical images is displayed, that is provided for observation by a user,
wherein said image processor, when the reduced image displayed on said reduced image display region and the observation image of the medical image displayed on said observation image display region are designated, as said process, selects a medical image at the substantially identical position to said designated observation image from said series of medical images based on stored image position information, and wherein said image processor instructs said image position adjusting component to adjust the position between said designated observation image and said selected medical image.

24. A medical image display apparatus according to claim 23, wherein
said plurality of image display regions further includes other observation image display regions in which an observation image of said series of tomographic images, and
said image processor instructs to display said designated observation image and an observation image of said selected medical image overlapping in which the position is adjusted by said image position adjusting component each other on said other observation image display region.

25. A medical image display apparatus according to claim 2, wherein
said incidental information includes image position information indicating the position of a medical image,
said image data storage component stores two or more different types of medical images, and
said medical image display apparatus is connected to a computer having an image position adjusting component operable to adjust positions of said different types of medical images, based on each image data of said different types of medical images and said image position information via a network,
wherein said medical image display apparatus further comprises
a reduced image generating component operable to generate image data of a reduced image of the medical image based on the image data of said medical image stored in said image data storage component, and
a communication component operable to communicate with said computer via said network,
wherein said plurality of image display regions includes a reduced image display region in which a reduced image generated for a representative image of a series of medical images is displayed and an observation image display region in which an observation image of the medical image having the same cross-sectional direction as said series of medical images and being different types of medical image from said series medical images is displayed, that is provided for observation by a user,
wherein said image processor, when the reduced image displayed on said reduced image display region and the observation image of the medical image displayed on said observation image display image are designated, selects a medical image at the substantially identical position to said designated observation image from said series of medical images based on stored image position information,
wherein said image processor instructs said communication component as said process to send to said computer via said network the image data of said designated observation image, the image data of said selected medical image, said stored image position information, and request information for requiring the position adjustment between said observation image and said medical image, so that said image position adjusting component adjusts the position between the observation image and the medical image.

26. A medical image display apparatus according to claim 25, wherein
said plurality of image display regions further includes other observation image display regions in which an observation image of said series of tomographic images, and
said image processor instructs to display said designated observation image and an observation image of said selected medical image overlapping in which the position is adjusted by said image position adjusting component each other on said other observation image display region.

27. A medical image display apparatus according to claim 2, wherein
said incidental information includes annotation information regarding an annotation image displayed attached to medical images,
said plurality of image display regions include a first observation image display region in which an observation image of the medical image provided for observation by a user is displayed and a second observation image display region in which an observation image of other medical image is displayed, and
said image processor, when the observation image of said medical image displayed on said first observation image display region and the annotation image displayed attached to the observation image of said other medical image displayed on said second observation image display region are designated, instructs as said process to display said designated said observation image attached by said designated annotation image on said first observation image display region, based on the annotation information regarding said designated annotation image.

28. A medical image display apparatus according to claim 2, wherein
said incidental information includes measurement information indicating the results of measurement implemented for a medical image,
said plurality of image display regions include a first observation image display region in which an observation image of the medical image provided for observation by a user is displayed and a second observation image display region in which an observation image of other medical images is displayed, and
said image processor, when the observation image of said medical image displayed on said first observation image display region and a measurement result image in connection with said measurement information displayed attached to the observation image of said other medical image displayed on said second observation image display region are designated, instructs as said process to display said designated observation image attached by said measurement result image on said first observation image display region based on the measurement information corresponding to said designated measurement result image.

29. A medical image display apparatus according to claim 1, further comprising:
a reduced image generating component operable to generate image data of a reduced image of the medical image based on the image data of said medical image stored in an image data storage component,
wherein said plurality of image display regions includes the reduced image display region in which a reduced image based on said generated image data is displayed and in the observation image display region in which an observation image of the medical image is displayed, the observation image being provided for observation by a user, and wherein said image processor, in response to designation of the reduced image displayed on said reduced image display region and the observation image displayed on said observation image display region, instructs as said process to terminate display of said designated observation image, and wherein said image processor instructs to display on said observation image display region the observation image in connection with the image data which is used for the image data of said designated reduced image.

30. A medical image display apparatus according to claim 1, further comprising:

a reduced image generating component operable to generate image data of a reduced image of the medical image based on the image data of said medical image stored in an image data storage component, wherein said plurality of image display regions includes the reduced image display region in which a reduced image based on said generated image data is displayed and the observation image display region in which an observation image of the medical image provided for observation by a user is displayed, and wherein said image processor, in response to designation of the reduced image displayed on said reduced image display region and the observation image displayed on said observation image display region, instructs as said process to display on said observation image display region the observation image in connection with the image data which is used for the image data of said designated reduced image, and said designated observation image.

31. A medical image display apparatus according to claim 1, comprising:

a mouse operable to designate, as a combination, one reduced image display region from the plurality of reduced image regions and one observation display region from the plurality of observation display regions, by dragging and dropping one or more medical images of said at least two medical images onto the other medical images.

32. A medical image display apparatus according to claim 1, wherein said image processor, when one or more medical images of said at least two medical images are designated, instructs to identifiably display the image display regions associated and not associated with processing contents by associating information, as a combination with the image display region in which said one or more medical images are displayed among said plurality of image display regions.

33. A medical image display apparatus according to claim 1, wherein associating information associates two or more said processing contents with the combination of the predetermined image display regions among said plurality of image display regions, and wherein said image processor, when the medical image displayed on one image display region of the combinations of said predetermined image display regions is designated, instructs to display the process selection information selectably presenting said two or more processing contents on said display component, and wherein said image processor instructs to execute the process indicated in the processing content selected from said two or more processing contents using said operation component.

34. A medical image display apparatus comprising:

a display component including a medical image display screen having a plurality of reduced image display regions and a plurality of observation display regions, each reduced image display region configured to show a reduced image of the medical image obtained by scanning of a medical image diagnosis apparatus, each observation display region configured to show in correspondence with each reduced image display region a medical image included in a same series as the medical image shown as the reduced image;

an image data storage component operable to store image data of medical images, an associating information storage component operable to store associating information for associating combinations of said image display regions with respective image processing to be performed on the image data of the medical images, an operation component, and a control component operable to instruct, when the medical images respectively displayed in a first image display region group of the reduced image display regions and a second image display region group of the observation display regions are designated using said operation component, to execute associated image processing of the image data of said designated medical images based on the combination of the first image display region group and the second image display region group and said associating information, wherein the associating information storage component is configured to associate each of a combination of a reduced image display region and an observation display region, a combination of reduced image display regions, and a combination of observation display regions with the image processing to be performed.

35. A medical image display apparatus according to claim 34, further comprising:

a reduced image generating component operable to generate image data of a reduced image of the medical image based on the image data of said medical image stored in said image data storage component, wherein said first image display region group includes a reduced image display region in which a reduced image based on said generated image data is displayed, said second image display region group includes an observation image display region in which an observation image of the medical image provided for observation by a user is displayed, and wherein said control component when the reduced image displayed on said reduced image display region and said observation image display region are designated, instructs as said process to terminate display of the observation image displayed on said observation image display region, and wherein said control component instructs to display on said observation image display region the observation image in connection with the image data which is used for the image data of said designated reduced image.

36. A medical image display apparatus according to claim 34, further comprising:

a reduced image generating component operable to generate image data of a reduced image of the medical image based on the image data of said medical image stored in said image data storage component, wherein said first image display region group includes a reduced image display region in which a reduced image based on said generated image data is displayed, said second image display region group includes an observation image display region in which an observation image of the medical image provided for observation by a user is displayed, and wherein said control component, when the reduced image displayed on said reduced image display region and said observation image display region are designated, instructs as said process to display on said observation image display region the observation image in connection with the image data which is used for the image data of said designated reduced image, together with the observation image displayed on said designated said observation image display region.

37. A medical image display apparatus according to claim 34, wherein said second image display region group includes only one image display region, said operation component comprises a mouse, and said mouse is operable for said designation by dragging and dropping the medical images respectively displayed on said first image display region group into said one image display region.

38. A medical image display apparatus according to claim 37, wherein said control component, when the medical image displayed on one image display region of said plurality of image display regions is dragged into other image display regions, instructs said display component to display the information of processing content indicating the processing content associated by said associating information with the combination of said one image display region and other image display regions.

39. A medical image display apparatus according to claim 34, wherein said control component, when the medical image displayed on one image display region of said plurality of image display regions is dragged into other image display regions, instructs said display component to display the information of processing content indicating the processing content associated by said associating information with the combination of said one image display region and other image display regions.

40. A medical image display apparatus according to claim 34, wherein said control component, when the medical images displayed on each of said first image display region group are designated, instructs to identifiably display the image display region associated and not associated with processing contents by said associating information as a combination of said first image display region group, among said plurality of image display regions.

41. A medical image display apparatus according to claim 34, wherein said associating information associates two or more of said processing contents with a combination of said first image display region group and said second image display region group, and wherein said control component, when the medical images each displayed on said first image display region group are designated, instructs said display component to display the process selection information selectably presenting said two or more processing contents, and wherein said control component instructs to execute the process indicated in the processing content selected via said operation component from said two or more processing contents.

42. A medical image display apparatus according to claim 41, wherein said control component, in response to an operation via said operation component, instruct said display component to display the operation content selection information selectably presenting two or more operation contents to be operated by said operation component.

43. A medical image display apparatus according to claim 34, wherein said control component, in response to an operation via said operation component, instruct said display component to display the operation content selection information selectably presenting two or more operation contents to be operated by said operation component.

\* \* \* \* \*